(12) United States Patent
Hill et al.

(10) Patent No.: US 11,617,511 B2
(45) Date of Patent: Apr. 4, 2023

(54) FLUOROLUCENT MAGNETIC FIELD GENERATOR

(71) Applicant: St. Jude Medical International Holding S.à r.l., Luxembourg (LU)

(72) Inventors: Anthony D. Hill, Minneapolis, MN (US); John Hauck, Shoreview, MN (US); Ryan M. Albu, Minneapolis, MN (US); Timothy G. Curran, St. Paul, MN (US); Ryan Link, Blaine, MN (US)

(73) Assignee: ST JUDE MEDICAL INTERNATIONAL HOLDINGS SARL, Grande-Duche (LU)

( * ) Notice: Subject to any disclaimer, the term of this patent is extended or adjusted under 35 U.S.C. 154(b) by 354 days.

(21) Appl. No.: 16/461,297

(22) PCT Filed: Nov. 21, 2017

(86) PCT No.: PCT/IB2017/057303
§ 371 (c)(1),
(2) Date: May 15, 2019

(87) PCT Pub. No.: WO2018/092114
PCT Pub. Date: May 24, 2018

(65) Prior Publication Data
US 2020/0060547 A1 Feb. 27, 2020

Related U.S. Application Data

(60) Provisional application No. 62/424,942, filed on Nov. 21, 2016, provisional application No. 62/424,972, (Continued)

(51) Int. Cl.
*A61B 5/00* (2006.01)
*A61B 5/06* (2006.01)
(Continued)

(52) U.S. Cl.
CPC ............ *A61B 5/0035* (2013.01); *A61B 5/062* (2013.01); *A61B 5/318* (2021.01); *A61B 6/12* (2013.01);
(Continued)

(58) Field of Classification Search
None
See application file for complete search history.

(56) References Cited

U.S. PATENT DOCUMENTS

| 512,340 A | 1/1894 | Tesla |
| 5,944,023 A | 8/1999 | Johnson et al. |

(Continued)

FOREIGN PATENT DOCUMENTS

| CN | 1681448 A | 10/2005 |
| CN | 104644169 A | 5/2015 |

(Continued)

*Primary Examiner* — Jermele M Hollington
*Assistant Examiner* — Suresh K Rajaputra
(74) *Attorney, Agent, or Firm* — Billion & Armitage

(57) ABSTRACT

A transmitting element for generating a magnetic field for tracking of an object includes a first spiral trace that extends from a first outer origin inward to a central origin in a first direction. A second spiral trace can extend from the central origin outward to a second outer origin in the first direction. The second spiral trace can extend from the central origin to the second outer origin in the first direction. The first spiral trace and the second spiral trace can be physically connected at the central origin to form the fluorolucent magnetic transmitting element and at least a portion of the first spiral trace overlaps at least a portion of the second spiral trace.

7 Claims, 18 Drawing Sheets

Related U.S. Application Data filed on Nov. 21, 2016, provisional application No. 62/424,950, filed on Nov. 21, 2016.

(51) Int. Cl.
- *A61B 6/00* (2006.01)
- *A61B 6/12* (2006.01)
- *G01B 7/00* (2006.01)
- *H01F 7/20* (2006.01)
- *H01F 27/28* (2006.01)
- *A61B 5/318* (2021.01)

(52) U.S. Cl.
CPC .............. *A61B 6/485* (2013.01); *G01B 7/003* (2013.01); *H01F 7/20* (2013.01); *H01F 27/2804* (2013.01)

(56) References Cited

U.S. PATENT DOCUMENTS

| | | |
|---|---|---|
| 6,177,792 B1 | 1/2001 | Govari et al. |
| 6,233,476 B1 | 5/2001 | Strommer et al. |
| 6,368,285 B1 | 4/2002 | Osadchy et al. |
| 6,493,573 B1 | 12/2002 | Martinelli et al. |
| 6,856,823 B2 | 2/2005 | Ashe |
| 7,197,354 B2 | 3/2007 | Sobe |
| 7,386,339 B2 | 6/2008 | Strommer et al. |
| 8,847,587 B2 | 9/2014 | Govari et al. |
| 9,024,624 B2 | 5/2015 | Brunner |
| 9,662,487 B2 | 5/2017 | Kveen et al. |
| 10,069,668 B2 | 9/2018 | Cohen et al. |
| 2003/0233042 A1 | 12/2003 | Ashe |
| 2007/0135803 A1 | 6/2007 | Belson |
| 2007/0197899 A1 | 8/2007 | Ritter et al. |
| 2008/0183071 A1 | 7/2008 | Strommer et al. |
| 2009/0082989 A1 | 3/2009 | Zuhars et al. |
| 2009/0233042 A1 | 9/2009 | Sadato et al. |
| 2010/0109848 A1 | 5/2010 | Blair et al. |
| 2010/0305427 A1* | 12/2010 | Huber et al. ........... A61B 34/20 600/424 |
| 2011/0224537 A1 | 9/2011 | Brunner |
| 2012/0029343 A1 | 2/2012 | Wasson et al. |
| 2014/0039302 A1 | 2/2014 | Miller et al. |
| 2014/0188133 A1 | 7/2014 | Misener |
| 2014/0200556 A1 | 7/2014 | Sela et al. |
| 2014/0275998 A1 | 9/2014 | Eichler et al. |
| 2015/0173643 A1 | 6/2015 | Govari et al. |
| 2015/0216490 A1 | 8/2015 | Ashe |
| 2016/0287133 A1* | 10/2016 | Eichler et al. ....... A61B 5/0044 |
| 2017/0087333 A1 | 3/2017 | Sela et al. |

FOREIGN PATENT DOCUMENTS

| | | |
|---|---|---|
| CN | 105813560 A | 7/2016 |
| EP | 0483698 A1 | 5/1992 |
| EP | 1891895 A1 | 2/2008 |
| JP | H03280511 A | 12/1991 |
| JP | 2002153443 A | 5/2002 |
| JP | 200878686 A | 8/2008 |
| WO | 2004006795 A1 | 1/2004 |
| WO | 2004091391 A1 | 10/2004 |
| WO | 2004061460 A3 | 7/2005 |
| WO | 2006121740 A2 | 11/2006 |
| WO | 2012090148 A1 | 7/2012 |
| WO | 2014052428 A1 | 4/2014 |
| WO | 2015068069 A1 | 5/2015 |
| WO | 2015071347 A1 | 5/2015 |

* cited by examiner

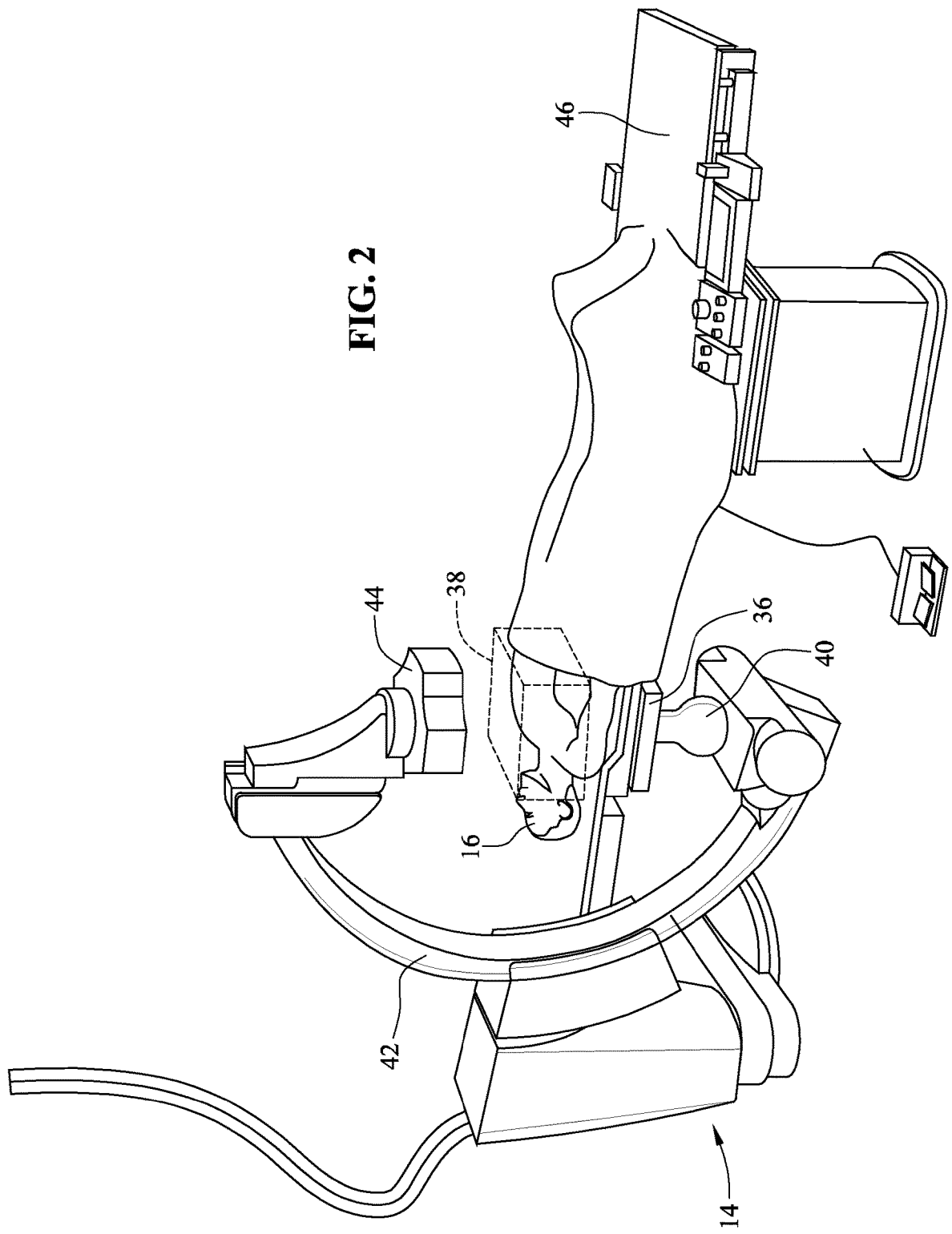

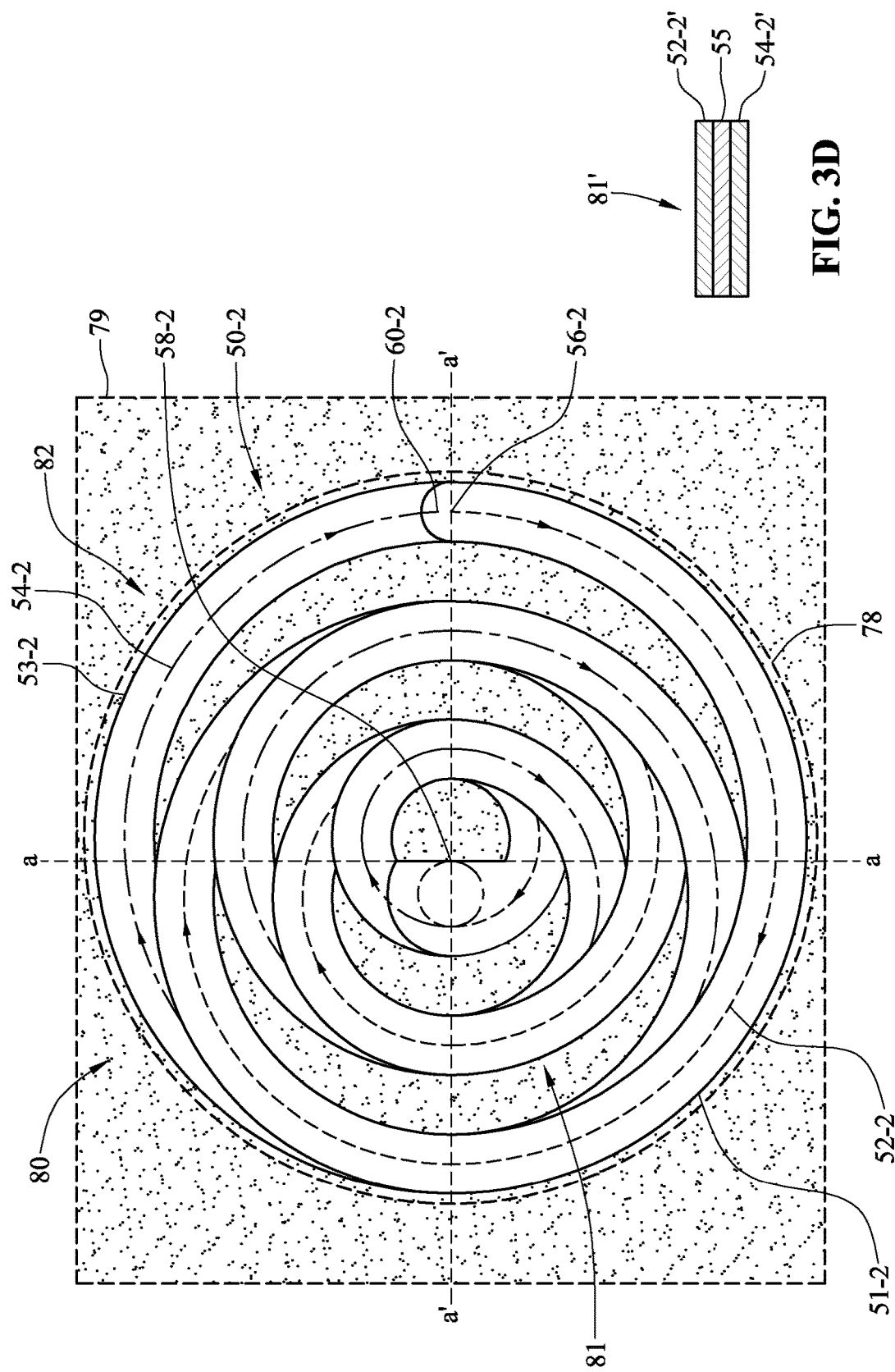

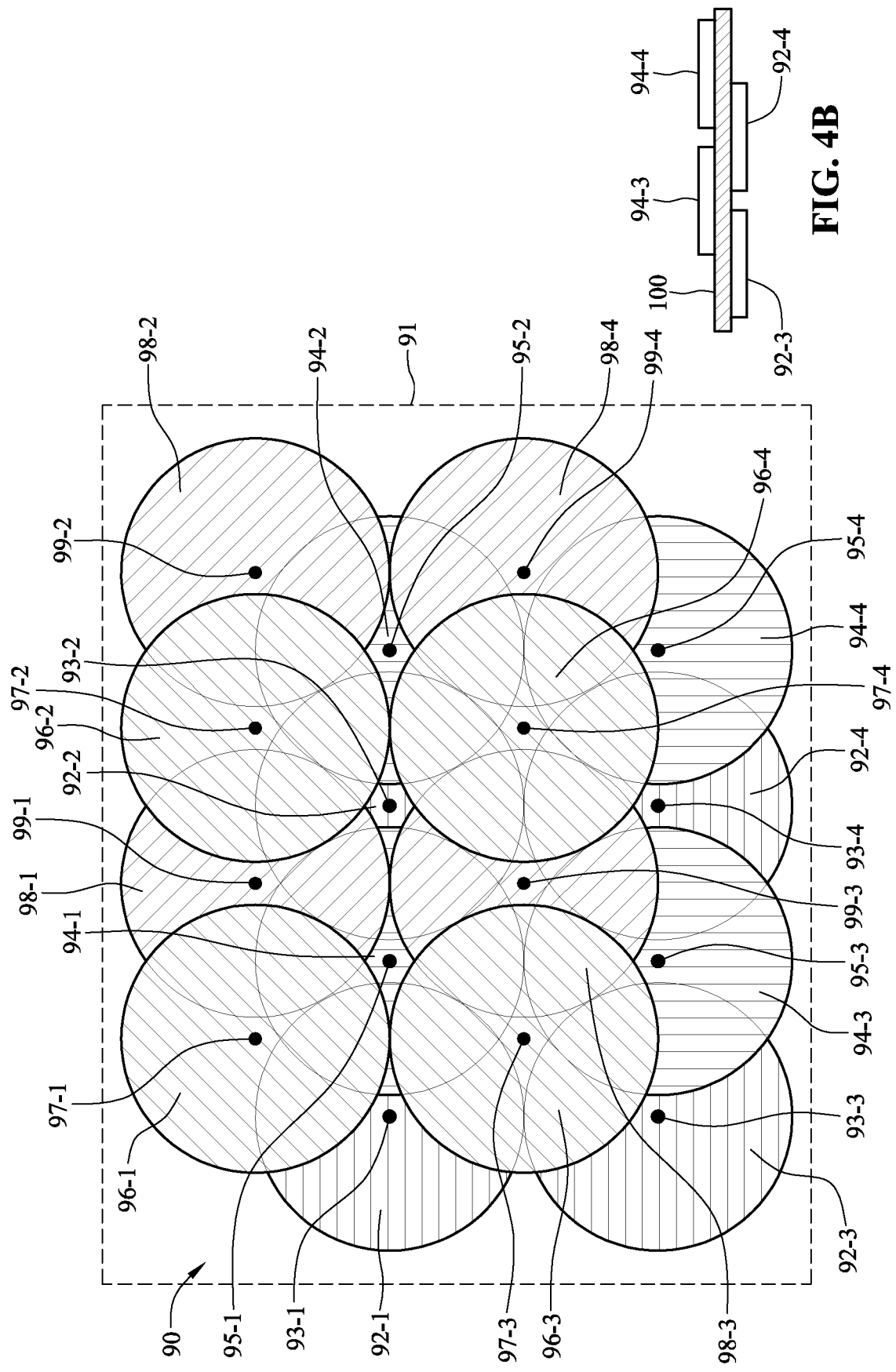

FLUOROLUCENT MAGNETIC FIELD GENERATOR

CROSS-REFERENCE TO RELATED APPLICATIONS

This application is a national stage filing based upon International application no. PCT/IB2017/057303, filed 21 Nov. 2017 and published in English on 24 May 2018 under International publication no. WO 2018/092114 (the '303 application), which claims priority to U.S. provisional application No. 62/424,972, filed 21 Nov. 2016 (the '972 application); and, U.S. provisional application No. 62/424,950, filed 21 Nov. 2016 (the '950 application); and, (3) U.S. provisional application No. 62/424,942, filed 21 Nov. 2016 (the '942 application). The '303 application; the '972 application; the '950 application; and the '942 application are all hereby incorporated by reference as though fully set forth herein.

BACKGROUND a. Field

The instant disclosure relates to a fluorolucent magnetic field generator and related components.

b. Background Art

Medical devices, catheters, and/or cardiovascular catheters, such as electrophysiology catheters can be used in a variety of diagnostic, therapeutic, mapping and/or ablative procedures to diagnose and/or correct conditions such as atrial arrhythmias, including for example, ectopic atrial tachycardia, atrial fibrillation, and/or atrial flutter. Arrhythmias can create a variety of conditions including irregular heart rates, loss of synchronous atrioventricular contractions and stasis of blood flow in a chamber of a heart, which can lead to a variety of symptomatic and asymptomatic ailments and even death.

A medical device can be threaded through a vasculature of a patient to a site where the diagnostic, therapeutic, mapping, and/or ablative procedure to diagnose and/or correct the condition is performed. To aid in the delivery of the medical device to the site, sensors (e.g., electrodes) can be placed on the medical device, which can receive signals that are generated proximate to the patient from a device (e.g., electromagnetic field generator). Based on the received signals, an orientation and/or position of the medical device can be computed.

SUMMARY

Various embodiments herein provide a fluorolucent magnetic transmitting element for generating a magnetic field for tracking of an object. The fluorolucent magnetic transmitting element includes a first spiral trace that extends from a first outer origin inward to a central origin in a first direction. A second spiral trace can extend from the central origin outward to a second outer origin in the first direction. The first spiral trace and the second spiral trace can be physically connected at the central origin to form the fluorolucent magnetic transmitting element and at least a portion of the first spiral trace is overlapped with at least a portion of the second spiral trace.

Various embodiments herein provide a fluorolucent magnetic transmitting element for generating a magnetic field for tracking of an object. A first fluorolucent magnetic transmitting element can be disposed in a first plane. A second fluorolucent magnetic transmitting element can be disposed in a second plane. The second fluorolucent magnetic transmitting element disposed in the second plane can partially overlap the first fluorolucent transmitting element disposed in the first plane.

Various embodiments herein provide a frame that includes a magnetic transmitting assembly. The frame can include a fluoro window. A first plurality of magnetic transmitting elements can be disposed on the frame on a first side of the fluoro window. A second plurality of magnetic transmitting elements can be disposed on the frame on a second side of the fluoro window. The second side can be disposed on an opposite side of the frame from the first side.

Various embodiments herein provide a method for preventing coil to coil coupling in an array of magnetic transmitting elements. A reference signal can be provided to a magnetic transmitting element and a low pass filter in parallel. The reference signal that has passed through the magnetic transmitting element can be sensed. A direct current offset can be generated with respect to the reference signal via the low pass filter. An attenuation signal can be generated by summing the direct current offset and the reference signal that has passed through the magnetic transmitting element. The attenuation signal can be applied to the reference signal to attenuate the reference signal.

Various embodiments can include a high frequency fluorolucent magnetic transmitting element drive circuit. The drive circuit can include a voltage input coupled to a Howland current source. The Howland current source can include an operational amplifier with an inverting input of the operational amplifier electrically coupled between a first and second modified Howland resistor and a non-inverting input of the operational amplifier electrically coupled between a third and fourth modified Howland resistor. The voltage input can be electrically coupled to the first modified Howland resistor. An output operational amplifier with a non-inverting input can be electrically coupled to an output of the Howland operational amplifier of the modified Howland current source and an inverting input electrically coupled to the fourth modified Howland resistor. An output of the second operational amplifier can be electrically coupled with a first resistor. A phase lead capacitor can be electrically coupled between an output of the output resistor and the second modified Howland resistor. A fluorolucent magnetic transmitting element can be coupled to the output of the output resistor.

Various embodiments can include a high frequency fluorolucent magnetic transmitting element drive circuit. A voltage input can be electrically coupled to a low-pass smoothing filter, wherein an output of the low-pass smoothing filter is electrically coupled to a non-inverting input of an operational amplifier. Various embodiments can include a modified Howland current source, wherein the modified Howland current source includes a Howland operational amplifier with an inverting input of the Howland operational amplifier electrically coupled between a first and second modified Howland resistor and a non-inverting input of the Howland operational amplifier electrically coupled between a third and fourth modified Howland resistor, and wherein an output of the operational amplifier is electrically coupled to the first modified Howland resistor. An output operational amplifier with a non-inverting input can be electrically coupled to an output of the Howland operational amplifier of the modified Howland current source and an inverting input can be electrically coupled to the fourth modified Howland resistor, wherein an output of the second operational amplifier is electrically coupled with an output resistor. A phase lead capacitor can be electrically coupled between an output of the output resistor and the second modified Howland resistor. A fluorolucent magnetic transmitting element can be electrically coupled to the output of the output resistor.

Various embodiments herein provide a method for determining an attenuation term for a signal produced by a fluorolucent magnetic transmitting element. The method can include driving the fluorolucent magnetic transmitting element with a first signal at a first frequency and a second signal at a second frequency to generate a first excitation signal and a second excitation signal, wherein the first frequency is lower than the second frequency. The method can include receiving a first received signal and a second received signal with a computer, the first received signal and the second received signal having been generated upon receipt of the first excitation signal and the second excitation signal with a magnetic position sensor. The method can include filtering the first received signal and the second received signal. The method can include determining an attenuation term for the second received signal at the second frequency based on the first filtered and received signal and the second filtered and received signal.

Various embodiments can include a non-transitory computer readable medium comprising computer executable instructions for determining an attenuation term for a signal produced by a fluorolucent magnetic transmitting element. The instructions can be executable by a processor to drive the fluorolucent magnetic transmitting element with a first signal at a first frequency and a second signal at a second frequency, wherein the first frequency is lower than the second frequency to generate a first excitation signal and a second excitation signal. The instructions can be executable by a processor to receive a first received signal and a second received signal with a computer, the first received signal and the second received signal having been generated upon receipt of the first excitation signal and the second excitation signal with a magnetic position sensor. The instructions can be executable by a processor to determine an attenuation term for the second received signal at the second frequency based on the first received signal and the second received signal. The instructions can be executable by a processor to apply the attenuation term to filter the attenuation term to provide a filtered attenuation term.

Various embodiments can include a system for determining an attenuation term for a signal produced by a fluorolucent magnetic transmitting element. The system can comprise a processor and a non-transitory computer readable medium comprising computer executable instructions, the instructions executable by the processor to drive the fluorolucent magnetic transmitting element with a first signal at a first frequency and a second signal at a second frequency to generate a first excitation signal and a second excitation signal, wherein the first frequency is lower than the second frequency. The instructions executable by the processor to receive a first received signal and a second received signal with a computer, the first received signal and the second received signal having been generated upon receipt of the first excitation signal and the second excitation signal with a magnetic position sensor. The instructions executable by the processor to determine an attenuation term for the second received signal at the second frequency based on the first received signal and the second received signal. The instructions executable by the processor to determine a position of the magnetic position sensor based on an attenuated received signal, the attenuated received signal having been generated through application of the attenuation term to the second received signal.

BRIEF DESCRIPTION OF THE DRAWINGS

FIG. 2 depicts a medical positioning system, in accordance with embodiments of the present disclosure.

FIG. 3C depicts a top view of the fluorolucent magnetic transmitting element in FIG. 3A after folding, in accordance with embodiments of the present disclosure.

FIG. 3D depicts a side view of a first spiral trace and a second spiral trace with an insulating material disposed therebetween, in accordance with embodiments of the present disclosure.

FIG. 4A depicts a top view of a magnetic transmitting array, in accordance with embodiments of the present disclosure.

FIG. 4B depicts a side view of an insulation layer disposed between a first layer of magnetic transmitting elements and a second layer of transmitting elements, in accordance with embodiments of the present disclosure.

DETAILED DESCRIPTION

In some embodiments, and with reference to FIG. 1, a system 10 can include a medical device 12 and a medical positioning system 14. The medical device 12 can include an elongate medical device such as, for example, a catheter or a sheath. For purposes of illustration and clarity, the description below will be limited to an embodiment wherein the medical device 12 comprises a catheter (e.g., catheter 12). It will be appreciated, however, that the present disclosure is not meant to be limited to such an embodiment, but rather in other exemplary embodiments, the medical device may comprise other elongate medical devices, such as, for example and without limitation, sheaths, introducers, guidewires, and the like.

Figure 1A:
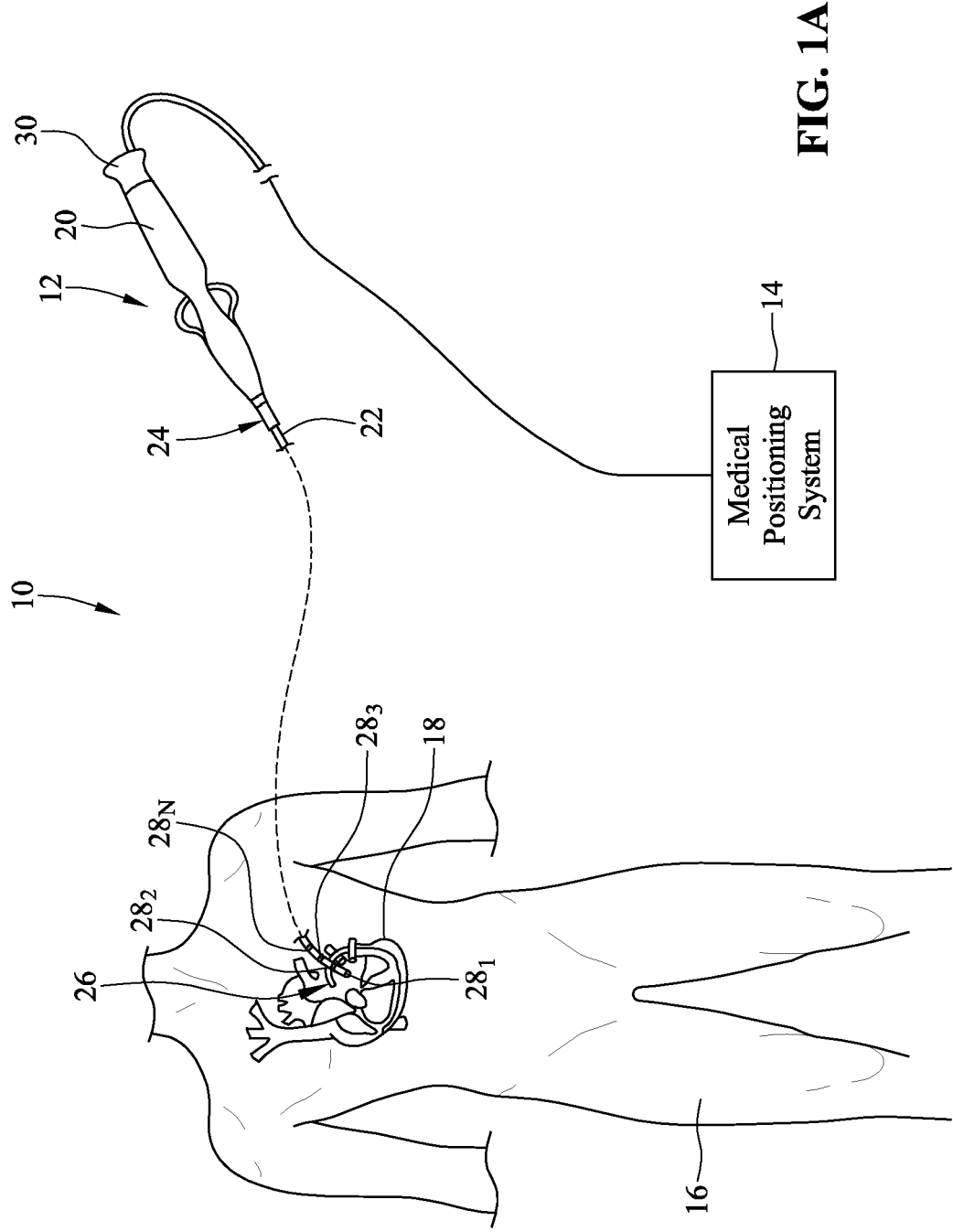
FIG. 1A depicts a diagrammatic view of an exemplary system for performing one or more diagnostic or therapeutic procedures, wherein the system comprises a magnetic field-based medical positioning system, in accordance with embodiments of the present disclosure.
Figure 1B:
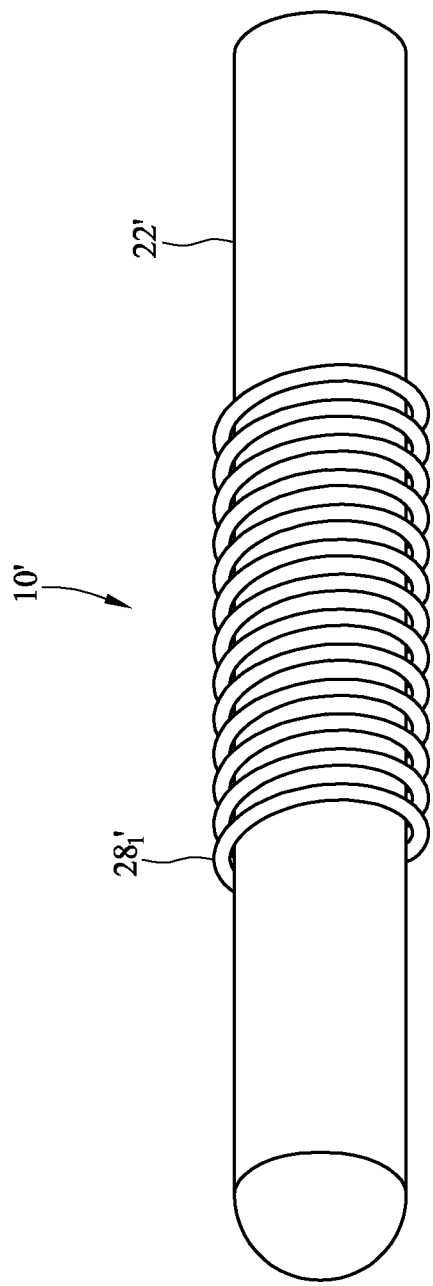
FIG. 1B depicts a magnetic position sensor disposed on a medical device for use in the magnetic field-based medical positioning system of FIG. 1A, in accordance with embodiments of the present disclosure.

With continued reference to FIG. 1, the catheter 12 can be configured to be inserted into a patient's body 16, and more particularly, into the patient's heart 18. The catheter 12 may include a handle 20, a shaft 22 having a proximal end portion 24 and a distal end portion 26, and one or more position sensors 28 mounted in or on the shaft 22 of the catheter 12. As used herein, "position sensor 28" or "position sensors 28" may refer to one or more position sensors $28_1$, $28_2$, $28_3$, . . . , $28_N$, as appropriate and as generally depicted. In an exemplary embodiment, the position sensors 28 are disposed at the distal end portion 26 of the shaft 22 and can be impedance based position sensors (e.g., electrodes) and/or magnetic based position sensors (e.g., a wound coil, as depicted and discussed in relation to FIG. 1B). For example, the position sensor $28_1$ can be a magnetic based position sensor and the position sensors $28_2$, $28_3$, . . . , $28_N$ can be impedance based position sensors. The catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

The shaft 22 can be an elongate, tubular, flexible member configured for movement within the body 16. The shaft 22 supports, for example and without limitation, sensors and/or electrodes mounted thereon, such as, for example, the position sensors 28, associated conductors, and possibly additional electronics used for signal processing and conditioning. The shaft 22 may also permit transport, delivery, and/or removal of fluids (including irrigation fluids, cryogenic ablation fluids, and bodily fluids), medicines, and/or surgical tools or instruments. The shaft 22 may be made from conventional materials such as polyurethane, and define one or more lumens configured to house and/or transport electrical conductors, fluids, or surgical tools. The shaft 22 may be introduced into a blood vessel or other structure within the body 16 through a conventional introducer. The shaft 22 may then be steered or guided through the body 16 to a desired location, such as the heart 18, using means well known in the art.

The position sensors 28 mounted in or on the shaft 22 of the catheter 12 may be provided for use in a variety of diagnostic and therapeutic purposes including, for example and without limitation, electrophysiological studies, pacing, cardiac mapping, and ablation. In an exemplary embodiment, one or more of the position sensors 28 are provided to perform a location or position sensing function. More particularly, and as will be described in greater detail below, one or more of the position sensors 28 are configured to provide information relating to the location (e.g., position and orientation) of the catheter 12, and the distal end portion 26 of the shaft 22 thereof, in particular, at certain points in time. Accordingly, in such an embodiment, as the catheter 12 is moved along a surface of a structure of interest of the heart 18 and/or about the interior of the structure, the position sensor(s) 28 can be used to collect location data points that correspond to the surface of, and/or other locations within, the structure of interest. These location data points can then be used for a number of purposes such as, for example and without limitation, the construction of surface models of the structure of interest.

For purposes of clarity and illustration, the description below will be with respect to an embodiment with a single position sensor 28. It will be appreciated, however, that in other exemplary embodiments, which remain within the spirit and scope of the present disclosure, the catheter 12 may comprise more than one position sensor 28 as well as other sensors or electrodes configured to perform other diagnostic and/or therapeutic functions. As will be described in greater detail below, the position sensor 28 can include a pair of leads extending from a sensing element thereof (e.g., a coil) that are configured to electrically couple the position sensor 28 to other components of the system 10, such as, for example, the medical positioning system 14.

FIG. 1B depicts a magnetic position sensor $28_1'$ disposed on a medical device 10' for use in the magnetic field-based medical positioning system of FIG. 1A, in accordance with embodiments of the present disclosure. The magnetic position sensor $28_1'$ can be a wound magnetic coil that is disposed along a shaft 22' of the medical device 10'. In some embodiments, the magnetic position sensor $28_1'$ can be disposed around an exterior of the shaft 22', as depicted. However, although not depicted, the magnetic position sensor $28_1'$ can be disposed within an interior lumen defined by the shaft 22' and/or within a wall of the shaft 22'.

With reference to FIGS. 1A to 2, the medical positioning system 14 will now be described in further detail. The medical positioning system 14 can be provided for determining a position and/or orientation of the position sensor 28 of the catheter 12, and thus, the position and/or orientation of the catheter 12. In some embodiments, the medical positioning system 14 may comprise a magnetic field-based system such as, for example, the MediGuide™ system from MediGuide Ltd. (now owned by St. Jude Medical, Inc.), and as generally shown with reference to one or more of U.S. Pat. Nos. 6,233,476; 7,197,354; and 7,386,339, the entire disclosures of which are incorporated herein by reference.

In some embodiments, and in general terms, the medical positioning system 14 comprises, at least in part, an apparatus 36 for generating a magnetic field for tracking of an object (e.g., catheter 12). The apparatus 36 can be configured to generate low-strength magnetic field(s) in and around the patient's chest cavity in an area of interest, which can be defined as a three-dimensional space designated as area of interest 38 in FIG. 2. In such an embodiment, and as briefly described above, the catheter 12 includes a position sensor 28, which is a magnetic position sensor configured to detect one or more characteristics of the low-strength magnetic field(s) applied by the apparatus 36 when the position sensor 28 is disposed within the area of interest 38.

The position sensor 28, which in an exemplary embodiment comprises a magnetic coil (e.g., as discussed in relation to FIG. 1B), can be electrically connected with a computer (e.g., processing core) and configured to generate a signal corresponding to the sensed characteristics of the magnetic field(s) to which the magnetic coil is exposed. The processing core can be responsive to the detected signal and can be configured to calculate a three-dimensional position and/or orientation reading for the position sensor 28. Thus, the medical positioning system 14 enables real-time tracking of each position sensor 28 of the catheter 12 in three-dimensional space, and therefore, real-time tracking of the catheter 12.

The medical positioning system 14 can utilize software, hardware, firmware, and/or logic to perform a number of functions described herein. The medical positioning system 14 can include a combination of hardware and instructions to share information. The hardware, for example can include a processing resource and/or a memory resource (e.g., non-transitory computer-readable medium (CRM) database, etc.). A processing resource, as used herein, can include a number of processors capable of executing instructions stored by the memory resource. The processing resource can be integrated in a single device or distributed across multiple devices. The instructions (e.g., computer-readable instructions (CRI)) can include instructions stored on the memory resource and executable by the processing resource for providing control over a magnetic field and/or performing the method 220 discussed in relation to FIG. 9, in an example The medical positioning system 14 can utilize software, hardware, firmware, and/or logic to perform a number of functions. The medical positioning system 14 can include a number of remote computing devices.

The medical positioning system 14 can be a combination of hardware and program instructions configured to perform a number of functions. The hardware, for example, can include one or more processing resources, computer readable medium (CRM), etc. The program instructions (e.g., computer-readable instructions (CRI)) can include instructions stored on CRM and executable by the processing resource to implement a desired function (e.g., determining an attenuation term for the second signal at the second frequency based on the filtered first signal). The CRI can also be stored in remote memory managed by a server and represent an installation package that can be downloaded, installed, and executed. The medical positioning system 14 can include memory resources, and the processing resources can be coupled to the memory resources. The processing resources can execute CRI that can be stored on an internal or external non-transitory CRM. The processing resources can execute CRI to perform various functions, including the functions described herein, for example, with respect to FIG. 9.

In some embodiments, the apparatus 36 can be located underneath a patient examination table 46, between an x-ray source 40 and the patient examination table 46. For example, the apparatus 36 can be connected with the patient examination table 46. In some embodiments, the apparatus 36 can be placed beneath the patient's body 16. For example, the apparatus 36 can be placed between the patient's body 16 and the patient examination table 46 (e.g., beneath a mattress. In some embodiments, the apparatus 36 can be placed within the patient examination table 46. In some embodiments, the apparatus 36 can be a mobile device, which can be placed on a chest of the patient and used to generate the magnetic field for tracking of the object.

In an example, challenges can be associated with generating a magnetic field for tracking an object, because the magnetic field can be distorted as a result of objects that are located proximate to the magnetic field and/or a generator that produces the magnetic field. For example, magnetic field-distorting components can be located proximately to a magnetic field generator (e.g., apparatus 36) and can include the x-ray source 40, portions of the patient examination table 46, a c-arm 42, and/or an x-ray image intensifier 44 associated with the medical positioning system 14. As such, the magnetic field-distorting components can have an effect on the magnetic field and cause distortions in the magnetic field. In some cases, even objects that are located far away from the magnetic field generator and/or the magnetic field produced by the magnetic field generator can cause distortions to the magnetic field. Part of the distortion can be to the magnetic field located within the area of interest 38. This can be problematic, because each position sensor 28 of the catheter 12 may benefit from a consistent (e.g., undistorted) magnetic field to determine a position and/or orientation of the position sensor 28 and/or catheter 12.

In an example, a source of the disturbance to the magnetic field can be an eddy current effect and/or a change in a magnetic permeability caused by magnetic field-distorting components. In an example, the magnetic field-distorting components can include conductive and/or magnetically permeable objects located within a proximity to the apparatus 36 and/or a magnetic field produced by the apparatus 36. In some examples, where the magnetic field-distorting component is stationary, an eddy current caused by the magnetic field-distorting component can be factored out when determining a location of the catheter 12, in an example, through calibration. However, in a medical positioning system 14, such as that depicted in FIG. 2, magnetic field-distorting components (e.g., x-ray source 40, c-arm 42, x-ray image intensifier 44, patient examination table 46) can move with respect to the apparatus 36 and can cause varying disturbances to the magnetic field produced by the apparatus 36, which can be unpredictable.

In some examples, the x-ray source 40 and the x-ray image intensifier 44 can be the greatest source of magnetic field distortion. Because the magnetic field-distorting components can move with respect to the apparatus 36, eddy currents produced by the magnetic field-distorting components can constantly vary and can be difficult to factor out (e.g., factor out a magnetic disturbance from a signal produced by a magnetic position sensor disposed in the magnetic field).

In some examples, the medical positioning system 14 can include an impedance-based system for determination of a position and/or orientation of the catheter 12. However, a distorted representation of a geometry of the heart can be generated when using an impedance-only based system, such as an Ensite™ system from St. Jude Medical, Inc. For instance, electrical currents used in an impedance based system can travel three-dimensionally along a path of least resistivity. As such, part of the electrical currents can leave a transverse plane with blood flow, for example, through an impedance transfer. Factoring in impedance transfer can involve a non-linear solution, which can result in the distorted representation of the geometry of the heart.

Accordingly, some embodiments of the present disclosure can reduce and/or eliminate distortions in the magnetic field produced by the apparatus 36 by reducing a strength of the magnetic field produced by the apparatus 36 in a vicinity of the magnetic field-distorting components. For example, the apparatus 36 can be moved within a close proximity to the area of interest 38 that is closer than thought possible. Thus, the magnetic field strength can be concentrated in the volume of interest 38. Accordingly, there can be less distortion of the magnetic field caused by distant objects. This can result in a reduction in the shift and/or drift associated with coordinates determined through the impedance-based system, as a result of the reduction and/or elimination of distortion in the magnetic field.

For example, a magnetic field generator that produces a magnetic field of a lesser magnitude can be placed proximate to the area of interest 38, such that a size of a magnetic field produced outside the area of interest 38 by the magnetic field generator is reduced, thus reducing chances for disturbance of the magnetic field by the magnetic field-distorting components.

Some embodiments of the present disclosure can lessen an effect that magnetic field-distorting components have on the magnetic field produced by the apparatus 36. For example, embodiments of the present disclosure can generate magnetic fields of multiple frequencies. The multiple frequencies can include a lower frequency and a higher frequency. The lower frequency field can remain unperturbated when magnetic field disturbing object(s) move within a proximity to the lower frequency field. The lower frequency can be used to calibrate the higher frequency in some embodiments to adjust for effects that the magnetic field-disturbing components have on the magnetic field of the higher frequency.

Magnetic tracking systems can employ a type of magnetic field generator that includes an arrangement of electrically excited coils. In the Mediguide™ system, this is referred to as a magnetic transmitter array (MTA). In previous systems, conventional coils (e.g., copper coils) can cause interference with a fluoroscopy image. For example, when conventional coils are placed between the patient and the fluoroscopy image beam and detector, the coils can appear on the fluoroscopy image, making it difficult to use the fluoroscopy image in catheter navigation.

Some embodiments of the present disclosure include an advantageous magnetic field generator, as described in more detail below. In some embodiments, the magnetic field generator can be fluorolucent. In an example, the magnetic field generator can be translucent in the fluoroscopy image and various instruments and/or anatomical features of the patient (e.g., heart) can be visible in the fluoroscopic image and are not obscured by the magnetic field generator in the fluoroscopic image. Fluorolucent can be defined as being translucent in a fluoroscopy image. For example, the fluorolucent magnetic field generator can be more translucent in a fluoroscopy image than a non-fluorolucent magnetic field generator of a same thickness formed from copper. This can make it easier for a physician to identify particular anatomical features and/or the catheter in the fluoroscopy image.

Figure 3A:
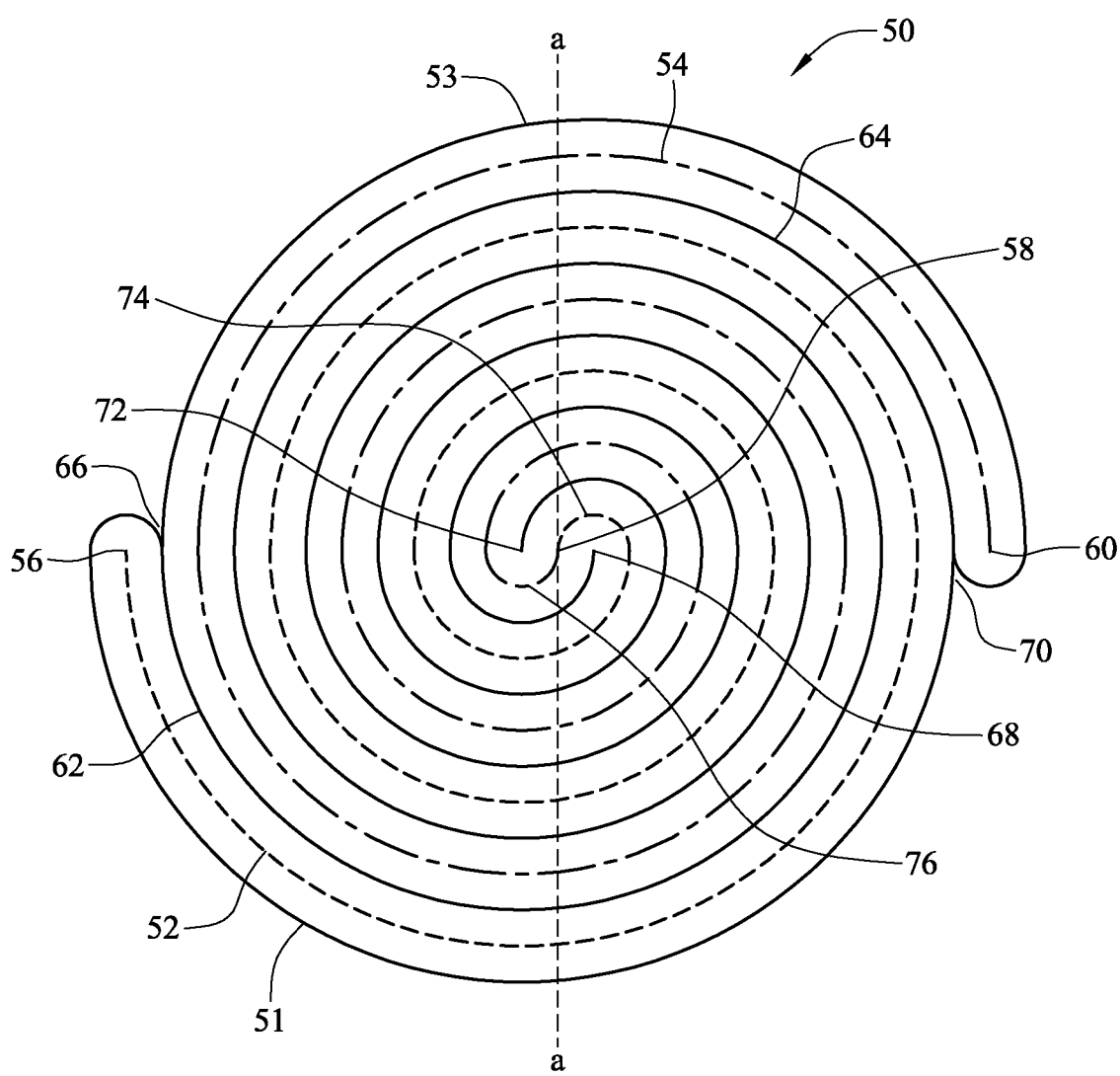
FIG. 3A depicts a top view of a fluorolucent magnetic transmitting element prior to being folded, in accordance with embodiments of the present disclosure.

FIG. 3A depicts a top view of a fluorolucent magnetic transmitting element 50 prior to being folded, in accordance with embodiments of the present disclosure. Some embodiments of the present disclosure can include a fluorolucent magnetic transmitting element 50 for generating a magnetic field for tracking of an object. For example, with further reference to FIG. 2, a catheter 12 equipped with a position sensor 28 can be placed within the area of interest 38 and the position sensor 28 can generate a particular signal depending on where the position sensor 28 is within the area of interest 38 (i.e., the magnetic field produced by the fluorolucent magnetic transmitting element 50).

To minimize an influence of magnetic field-distorting components (e.g., c-arm movement), it can be desirable to move the fluorolucent magnetic transmitting element 50 (e.g., transmitter coils) as close as possible to the navigational domain The magnitude of metallic interference is a function of both the distances between the fluorolucent magnetic transmitting element 50 and position sensor 28 (e.g., coil) and between the transmitting element and field-distorting component. Conventional transmitter coils (e.g., copper wound coils) can only be placed so close to the navigational domain before the conventional transmitter coils themselves appear in the fluoroscopic image, obscuring clinically relevant details and limiting the clinical utility of the primary imaging modality. In an example, conventional transmitter coils may be placed no closer than 30 centimeters of the navigational domain, before the conventional transmitter coils appear in the fluoroscopic image. For instance, the material (e.g., copper) from which the conventional transmitter coil is formed can begin to scatter X-ray photons and appears in the fluoroscopic image when the conventional transmitter coil is placed closer than 30 centimeters to the navigational domain.

In contrast, transmitter coils of the present disclosure can be planar and can be made thin enough to lie directly beneath a patient. For example, in some embodiments of the present disclosure, the fluorolucent magnetic transmitting element 50 can be formed from a planar substrate. In an example, the fluorolucent magnetic transmitting element 50 can include planar coils that can be made thin enough to lie directly beneath a patient. In some embodiments, the fluorolucent magnetic transmitting element 50 can be disposed between a mattress and table, as described in U.S. application Ser. No. 15/034,474, which is hereby incorporated by reference as though fully set forth herein. In some embodiments, the fluorolucent magnetic transmitting element 50 can be placed within 5 centimeters of the navigational domain A maximum dimension of the fluorolucent magnetic transmitting element 50 can be defined at an upper limit by a size of a patient examination table 46 and/or defined by a number of fluorolucent magnetic transmitting elements 50 that need to be placed in proximity to the navigational domain (e.g., area of interest 38) in order to create a number of different signals for receipt by the position sensor 28.

With reference to magnetic transmitting elements formed of copper (e.g., copper magnetic transmitting element), an amount of energy that can be dissipated from the copper magnetic transmitting element in the form of heat can be limited by a thickness of a mattress associated with the patient examination table 46. For example, the patient examination table 46 can include a frame and a mattress that has a multiplicity of layers or heavy layer weights associated with the mattress that act as an insulator. The copper magnetic transmitting element can be disposed between the mattress and the frame. The mattress can insulate a patient from heat produced by the copper magnetic transmitting element and the heat produced by the copper magnetic transmitting element can be dissipated through the frame, which can act as a conductor. An amount of copper included in the copper magnetic transmitting element can be increased, thus decreasing a resistance associated with the copper magnetic transmitting element and decreasing an amount of heat generated by the magnetic transmitting element as a current flows through the transmitting element.

As a result of a standard thickness associated with a mattress, copper magnetic transmitting elements can be made with enough copper that while the copper magnetic transmitting element produces an amount of heat that can be dissipated by the frame of the patient examination table 46 and insulated from the patient by the mattress; the amount of copper with which the transmitting element is made causes it to be visible on a fluoroscopy image, oftentimes obscuring the fluoroscopy image. In contrast, embodiments of the present disclosure can provide a fluorolucent magnetic transmitting element made with enough fluorolucent material (e.g., aluminum), such that a standard thickness mattress can insulate a patient from heat produced by the fluorolucent magnetic transmitting element, while the fluorolucent magnetic transmitting element remains fluorolucent in the fluoroscopy image.

The fluorolucent magnetic transmitting element 50 can include a first spiral trace 52 and a second spiral trace 54. In some embodiments, the spiral traces can be formed on a first spiral arm 51 and a second spiral arm 53. For example, the first spiral trace 52 can be formed on the first spiral arm 51 and the second spiral trace 54 can be formed on the second spiral arm 53. In some embodiments, the first spiral arm 51 and the second spiral arm 53 can be formed from an insulative material (e.g., polyimide) and the first spiral trace 52 and the second spiral trace 54 can be formed on a surface of the insulative material.

In some embodiments, as further discussed herein, the first spiral arm 51 and the second spiral arm 53 can be formed from an insulative material and/or fluorolucent material (e.g., a polymer) and the first spiral trace 52 and the second spiral trace 54 can be formed in an interior of the first spiral arm 51 and the second spiral arm 53. For example, the first spiral arm 51 and the second spiral arm 53 can be a coating that surrounds the first spiral trace 52 and the second spiral trace 54. In some embodiments, the first spiral trace 52 and the second spiral trace 54 can be disposed on a polymer, such as a polyimide. The first spiral trace 52 and the second spiral trace 54 can be sandwiched between the polyimide and an insulating epoxy solder mask to form the first spiral arm 51 and the second spiral arm 53. Alternatively, in some embodiments, the first spiral arm 51 and the second spiral arm 53 can act as the first spiral trace 52 and the second spiral trace 54, respectively. For example, the first spiral arm 51 and the second spiral arm 53 can be formed from a conductive fluorolucent material (e.g., aluminum). As further discussed herein, when referring to the first spiral trace 52 and the second spiral trace 54, this can include the first spiral arm 51 and the second spiral arm 53 when the first spiral arm 51 and the second spiral arm 53 are formed from a conductive fluorolucent material.

In embodiments of the present disclosure, a substrate such as aluminum is used to create the spiral traces 52, 54. Although aluminum has approximately 60 percent of the electrical conductivity of copper, it has approximately 30 percent the density of copper and atomic nuclei that are lighter, resulting in fluorolucency of the fluorolucent magnetic transmitting element 50 in a fluoroscopy image (e.g., a greatly reduced x-ray footprint or visibility). The fluorolucency is attained at thicknesses of the fluorolucent magnetic transmitting element 50 that yield comparable electrical resistance to a copper magnetic transmitting element of the same size and/or thickness. In some embodiments of the present disclosure, the fluorolucent magnetic transmitting element 50 can provide advantages when used in conjunction with magnetic resonance imaging (MRI). For example, the fluorolucent magnetic transmitting element 50 can be compatible with magnetic fields produced via MRI and can be sized such that the fluorolucent magnetic transmitting element 50 and/or an array of fluorolucent magnetic transmitting elements fits inside of an MRI scanner tube, when in position under a patient.

In some embodiments of the present disclosure, a first spiral trace 52 extends from a first outer origin 56 inward to a central origin 58. The first spiral trace 52 can form one or more loops around the central origin 58 as it extends inward toward the central origin 58. As depicted in FIG. 3A, the first spiral trace 52 can form approximately two and a half loops around the central origin 58. However, more than two and a half loops or less than two and a half loops can be formed by the first spiral trace 52 around the central origin 58 in some embodiments. In some embodiments, the first spiral trace 52 can extend from the first outer origin 56 to the central origin 58 in a first direction. For example, as depicted, the first spiral trace 52 can extend from the first outer origin 56 to the central origin 58 in a counterclockwise direction.

In some embodiments, the second spiral trace 54 can extend from the central origin 58 outward to a second outer origin 60. The second spiral trace 54 extends from the central origin 58 to the second outer origin 60 in a second direction that is opposite of the first direction. In some embodiments, the fluorolucent magnetic transmitting element 50 can be formed from a planar piece of material (e.g., fluorolucent material). The planar piece of material can be cut between the first spiral trace 52 and the second spiral trace 54 to the central origin 58. For example, a first cut 62 and a second cut 64 can be formed in the fluorolucent magnetic transmitting element 50 between the first spiral trace 52 and the second spiral trace 54. The first cut 62 can be formed between the first outer origin 56 and the second spiral trace 54, in some embodiments. For example, the first cut 62 can originate from a first origination point 66 and can terminate at a first termination point 68. The second cut 64 can be formed between the second outer origin 60 and the first spiral trace 52, in some embodiments. For example, the second cut 64 can originate from a second origination point 70 and can terminate at a second termination point 72.

In some embodiments, an amount of material can be left at the central origin so the first spiral trace 52 and the second spiral trace 54 remain connected at the central origin 58. For example, material can be left between the first termination point 68 of the first cut 62 and the second termination point 72 of the second cut 64. As such, the first spiral trace 52 and the second spiral trace 54 can be formed from a continuous piece of material and no joints can exist between the first spiral trace 52 and the second spiral trace 54. In an example, no joints exists between a first inner origin 74 of the first spiral trace 52 and a second inner origin 76 of the second spiral trace 54. For instance, a connection can be formed between the first inner origin 74 and the second inner origin 76 by a continuous trace of material. As such, embodiments of the present disclosure can avoid joining the circuit elements (e.g., first spiral trace 52, second spiral trace 54) at the first inner origin 74 and the second inner origin 76 by soldering, welding, wire-bonding, electroplating throughholes, vias, etc.

In some embodiments, the fluorolucent magnetic transmitting element 50 can be formed via a forging, casting, cutting, machining, or other process. For example, the fluorolucent magnetic transmitting element 50 can be formed such that slits are defined between the first spiral trace 52 and the second spiral trace 54. The fluorolucent magnetic transmitting element 50 can be formed from a sheet of aluminum, in some embodiments. Alternatively, the fluorolucent magnetic transmitting element 50 can be formed from substrates other than aluminum. In some embodiments, the fluorolucent magnetic transmitting element 50 can be formed from another type of fluorolucent material. In an example, the fluorolucent magnetic transmitting element 50 can be formed from a fluorolucent material such as silver printed ink or carbon graphene.

While some embodiments of the present disclosure can form the fluorolucent magnetic transmitting element 50 via subtractive methods, such as cutting, machining, etc., additive type methods can also be used for form the fluorolucent magnetic transmitting element 50, such as depositing of fluorolucent material in a particular patter via deposition, printing, etc. In some embodiments, the fluorolucent magnetic transmitting element 50 can be printed with silver printed ink, for example, with a three-dimensional printer. Alternatively, in some embodiments, a planar layer of carbon graphene can be cut to form the first spiral trace 52 and the second spiral trace 54. In some embodiments, one or more layers of carbon graphene can be laid to form the first spiral trace 52 and the second spiral trace 54. As such, the first spiral trace 52 and the second spiral trace 54 can be formed without cutting.

Figure 3B:
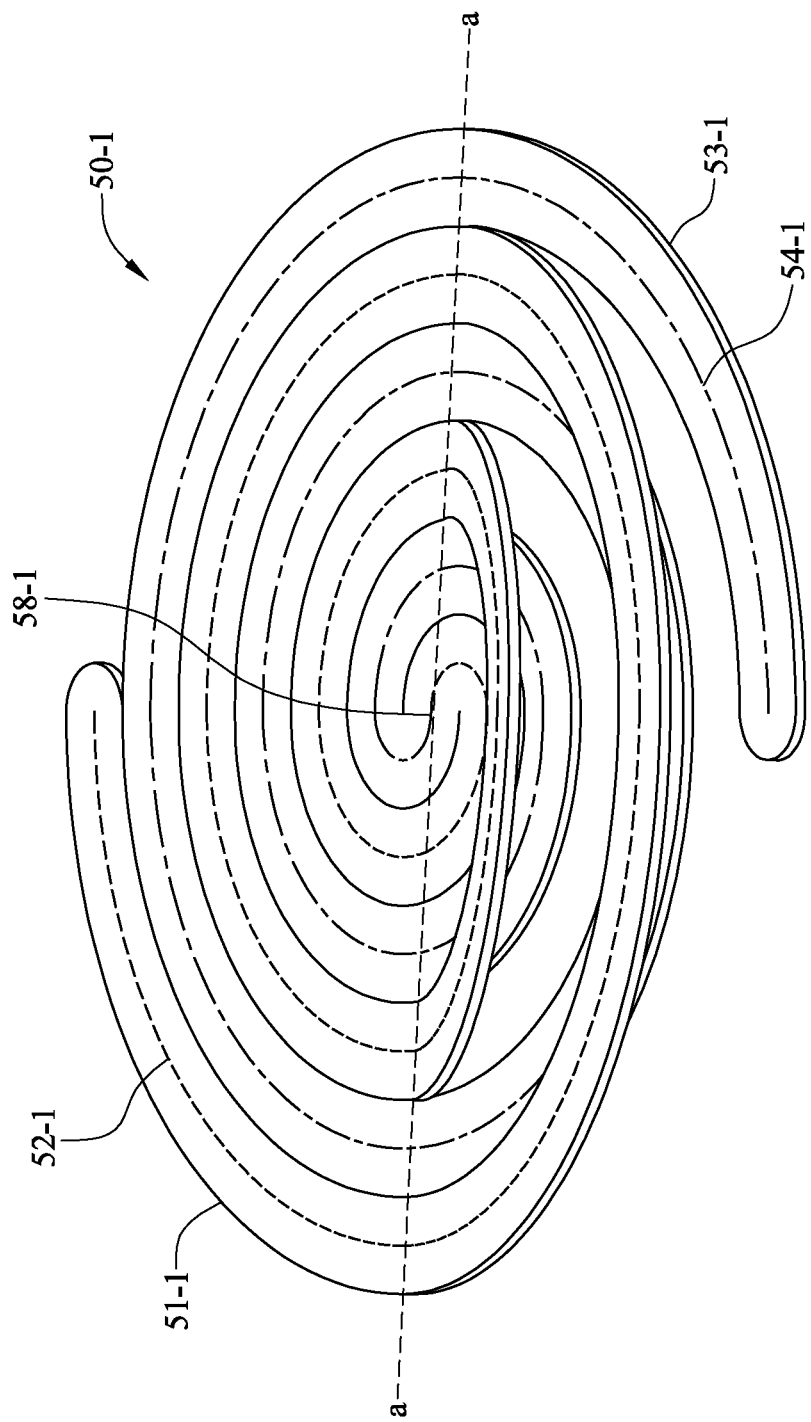
FIG. 3B depicts an isometric side view of the fluorolucent magnetic transmitting element in FIG. 3A partially folded, in accordance with embodiments of the present disclosure.

FIG. 3B depicts an isometric side view of the fluorolucent magnetic transmitting element in FIG. 3A partially folded, in accordance with embodiments of the present disclosure. In some embodiments, the fluorolucent magnetic transmitting element 50-1 can be folded across an axis defined by line aa at the central origin. The axis aa can extend across the fluorolucent magnetic transmitting element 50-1, such that the axis aa divides the fluorolucent magnetic transmitting element 50-1 in half and the first outer origin 56 and the second outer origin 60 are diametrically opposed to one another. For example, as depicted in FIG. 3B, the fluorolucent magnetic transmitting element 50-1 is folded across the axis aa at the central origin 58-1.

The continuous piece of material that forms the first spiral trace 52-1 and the second spiral trace 54-1 and that also forms the first spiral arm 51-1 and the second spiral arm 53-1 can be folded at the central origin 58-1. As depicted, the first spiral trace 52-1 and the second spiral trace 54-1 are being folded along the axis aa at the central origin 58-1. In an example, the fluorolucent magnetic transmitting element 50-1 can be folded at the central origin 58-1, such that a crease only occurs at the central origin 58-1 along axis aa. In some embodiments care must be taken to prevent the fluorolucent magnetic transmitting element from breaking along the crease. For example, a mandrel can be used when forming the crease at the central origin 58-1 along axis aa. The fluorolucent magnetic transmitting element 50-1 can be folded at the central origin 58-1 such that the first spiral trace 52-1 is rotated 180 degrees about the axis aa, alternatively, the second spiral trace 54-1 can be rotated 180 degrees about the axis aa. In an example, upon folding the fluorolucent magnetic transmitting element 50-1, portions of each spiral trace 52-1, 54-1 not located at the central origin 58-1 along axis aa may not be creased.

FIG. 3C depicts a top view of the fluorolucent magnetic transmitting element 50-2 in FIG. 3A after folding, in accordance with embodiments of the present disclosure. For purposes of illustration, the fluorolucent magnetic transmitting element 50-2 is depicted on a background 79 to help demonstrate the fluorolucent magnetic transmitting element 50-2. In some embodiments, when the fluorolucent magnetic transmitting element 50-2, as depicted in FIG. 3A, is folded along the axis aa at the central origin 58-2, the first spiral trace 52-2 can overlap with (e.g., be stacked on top of) an area of the second spiral trace 54-2. For example, the first spiral trace 52-2 can overlap the second spiral trace 54-4 at overlapping area 81. Although overlapping area 81 is discussed herein, multiple portions of the first spiral trace 52-2 and the second spiral trace 54-4 can overlap, as depicted. As used with respect to FIGS. 3A, 3B, and 3C, the fluorolucent magnetic transmitting element 50 is in an unfolded state, the fluorolucent magnetic transmitting element 50-1 is in a partially folded state, and the fluorolucent magnetic transmitting element 50-2 is in a folded state.

In some embodiments, the first spiral trace 52-2 and/or the second spiral trace 54-2 can be rotated (e.g., 180 degrees) about the axis aa, such that a crease is formed between the first spiral trace 52-2 and the second spiral trace 54-2 along the axis aa. For example, the first spiral trace 52-2 can overlap the second spiral trace 54-2 on a first side 80 of the axis aa and the second spiral trace 54-2 can overlap the first spiral trace 52-2 on a second side 82 of the axis aa. In some embodiments, a first electrical terminal (also referred to herein as first outer origin) can be disposed at a first outer origin 56-2 of the first spiral trace 52-2 and a second electrical terminal (also referred to herein as second outer origin) can be disposed at a second outer origin 60-2 of the second spiral trace 54-2.

In some embodiments, a current can be supplied to the first electrical terminal or the second electrical terminal and the current can flow through the fluorolucent magnetic transmitting element 50-2. If current is supplied to the first electrical terminal at the first outer origin 56-2, the current can flow clockwise, as depicted by the arrows in FIG. 3C, along the first spiral trace 52-2 toward the central origin 58-2 and then the current can flow from the central origin 58-2 along the second spiral trace 54-2, also in a clockwise direction, as further depicted by the arrows in FIG. 3C, toward the second outer origin 60-2 and the second electrical terminal at the second outer origin 60-2. As such, the current can flow through the fluorolucent magnetic transmitting element 50-2 from the first electrical terminal to the second electrical terminal in a clockwise direction and can produce a magnetic field.

Alternatively, current can be supplied to the second electrical terminal at the second outer origin 60-2. The current can flow counter-clockwise along the second spiral trace 54-2 toward the central origin 58-2 and then the current can flow from the central origin 58-2 along the first spiral trace 52-2, also in a counter-clockwise direction toward the first outer origin 56-2 and the second electrical terminal at the first outer origin 56-2. As such, the current can flow through the fluorolucent magnetic transmitting element 50-2 from the first electrical terminal to the second electrical terminal in a counter-clockwise direction and can produce a magnetic field.

Although the description of FIG. 3C references a fluorolucent magnetic transmitting element, the configuration can be beneficial for a non-fluorolucent magnetic transmitting element (e.g., a magnetic transmitting element formed of a non-fluorolucent material such as copper), as well. In an example, a uniform current direction is maintained by the configuration depicted in FIG. 3C, while the electrical terminals (e.g., first outer origin 56-2 and second outer origin 60-2) are located at an outer portion of the transmitting element. Some transmitting elements can maintain a uniform current direction, however, one electrical terminal is located on an outside of the transmitting element and one electrical terminal can be located at a central origin of the transmitting element, thus making electrical connection of the transmitting element more difficult. Embodiments of the present disclosure can avoid this difficulty. However, some embodiments, of the present disclosure can include a magnetic transmitting element that is formed of a fluorolucent material that includes one electrical terminal located on an outside of the transmitting element. A trace of the magnetic transmitting element can be coiled inward from the electrical terminal located on the outside of the transmitting element towards a central origin and can terminate at an inner terminal.

Some embodiments of the present disclosure can include a magnetic transmitting assembly as discussed in relation to U.S. application Ser. No. 15/034,474, which is hereby incorporated by reference as though fully set forth herein, that is made from a fluorolucent material (e.g., aluminum).

FIG. 3D depicts overlapping area 81' that includes a first spiral trace 52-2' and a second spiral trace 54-2' and an insulating material 55 disposed between the first spiral trace 52-2' and the second spiral trace 54-2'. For example, an insulating material can be disposed between the overlapping area 81' of the first spiral trace 52-2' and the second spiral trace 54-2'. In some embodiments, the insulating material can prevent the first spiral trace 52-2' and the second spiral trace 54-2' contacting one another, causing a disturbance to the flow of current. In an example, the insulating material can prevent a short from occurring where the first spiral trace 52-2' and the second spiral trace 54-2' overlap, allowing for the current to flow completely through the first spiral trace 52-2' and the second spiral trace 54-2'.

In some embodiments, although not depicted, each spiral trace 52-2', 54-2' can be coated in an insulated material. For example, a top, bottom, and opposing lateral sides of each spiral trace 52-2', 54-2' can be coated in an insulated material. Accordingly, as the first spiral trace 52-2' and second spiral trace 54-2' are creased at their central origin and the first spiral trace 52-2' and the second spiral trace 54-2' overlap one another, the first spiral trace 52-2' and the second spiral trace 54-2' can remain electrically isolated from one in the overlapping area 81', due to the insulative coating on each of the first spiral trace 52-2' and the second spiral trace 54-2' being disposed between the traces.

With further reference to FIG. 3C, in an example, a magnetic field can be generated by the fluorolucent magnetic transmitting element 50-2. The current can flow through the fluorolucent magnetic transmitting element 50-2 in a uniform direction from the first electrical terminal to the second electrical terminal or from the second electrical terminal to the first electrical terminal, as previously discussed herein. For example, the current can flow in a uniform direction, as indicated by the arrows depicted in FIG. 3C.

Although the fluorolucent magnetic transmitting element 50-2 is depicted as generally circular in shape, the fluorolucent magnetic transmitting element 50-2 can be square, rectangular, triangular, polygonal, oval, elliptical, etc. In an example, the maximum dimension of the fluorolucent magnetic transmitting element 50-2 can be defined by the circle 78 that is depicted in phantom in FIG. 3C. In an example, the circle 78 can have a diameter in a range from 6 to 14 centimeters. However, the diameter of the circle 78 can be greater than 14 centimeters and less than 6 centimeters in some embodiments. Regardless of whether the fluorolucent magnetic transmitting element 50-2 is square, rectangular, triangular, polygonal, etc., the magnetic transmitting element 50-2 magnetic transmitting element can have a maximum dimension such that it fits within the circle 78, in some embodiments. For purposes of illustration and to distinguish the circle 78 from the fluorolucent magnetic transmitting element 50-2, the circle 78 is depicted as having a larger diameter than the fluorolucent magnetic transmitting element. Embodiments of the present disclosure can include a fluorolucent magnetic transmitting element with a maximum dimension that is the same as a diameter of the circle 78.

The continuous piece of substrate that forms the fluorolucent magnetic transmitting element 50-2 allows for the current to continuously pass through the fluorolucent magnetic transmitting element 50-2 without the use of any joints. Some prior approaches have employed processes to manufacture planar magnetic transmitters using printed circuit board processes. A number of vias can be produced between segments of printed circuit board to form spiral traces and to join multiple spiral traces together, such that current can continuously flow through the spiral traces. Due to a greater reactivity of aluminum, electroplating vias can be ineffective when the substrate or a portion of the substrate is formed from aluminum.

Embodiments of the present disclosure can allow for a first spiral trace 52-2 and a second spiral trace 54-2 to be formed from a unitary piece of material, as discussed herein, while providing a fluorolucent magnetic transmitting element 50-2 that can provide for a unidirectional current flow. For example, folding the first spiral arm 51-2 (e.g., first spiral trace 52-2) and the second spiral arm 53-2 (e.g., second spiral trace 54-2) of the fluorolucent magnetic transmitting element 50-2 at the central origin 58-2 can allow for the first spiral arm 51-2 (e.g., first spiral trace 52-2) and the second spiral arm 53-2 (e.g., second spiral trace 54-2) to be formed from a unitary piece of material. Thus, embodiments of the present disclosure can avoid use of vias or other types of connectors to join segments and multiple spiral traces together. For example, embodiments of the present disclosure can utilize a single piece of material (e.g., aluminum) to form the magnetic transmitting element. While a first spiral trace 52-2 and a second spiral trace 54-2 are discussed as two traces, the first and second traces 52-2, 54-2 are formed from a unitary piece of material, thus avoiding the use of vias.

FIG. 4A depicts a top view of a magnetic transmitting array 90 that includes a set of magnetic transmitting elements 92-1, 92-2, 92-3, 92-4, 94-1, 94-2, 94-3, 94-4, 96-1, 96-2, 96-3, 96-4, 98-1, 98-2, 98-3, and 98-4, in accordance with embodiments of the present disclosure. Some embodiments of the present disclosure can prevent neighboring magnetic drive coils from coupling with each other. In an example, multiple drive coils can be used to provide sufficient spatially-unique and orientation-unique signaling at any point in 3D space where it is desired to determine the location and orientation of a position sensor 28 (e.g., magnetic sensing coil). The unique signals can be created using a specific frequency to excite each magnetic drive coil, although time domain methods could also be employed. A sense coil amplifier and signal processor then measure a unique amplitude value attributable to each drive coil (in the case of frequency division multiplexing, synchronous demodulation for example is used). It is important that excitation from one drive coil does not couple into adjacent drive coils, and then radiate from those coils, as this can confound the subsequent means to derive accurate location of the magnetic sensing coil. Assuming each coil is excited by a unique frequency, the desired physical behavior which leads to the simplest mathematical model is that each frequency only represents emanation from a single drive coil at its location. Coupling and re-radiating a signal (e.g., excitation signal) from neighboring coils is undesirable, as this can confound the mathematical model.

To locate and orient a magnetic position sensor 28 (e.g., magnetic sensing coil), 3 degrees of freedom (e.g., x, y, z) for the location can be desired and 2 degrees of freedom (e.g., pitch and yaw) for the orientation. This means that a minimum of 5 drive coils may be required. In some embodiments, more coils can be useful for solving for additional parameters such as system gain, or for extending the viable sensing region. In some embodiments, coils with a low inductance may be susceptible to coupling with neighboring coils and re-radiating the signal from neighboring coils. Embodiments of the present disclosure can reduce and/or eliminate coupling between neighboring coils. In some embodiments of the present disclosure, the fluorolucent magnetic transmitting element, as discussed in relation to FIG. 3C, can include one layer of substrate, for example, when the magnetic transmitting element is made from aluminum. To increase a number of layers, the magnetic transmitting array 90 can include a number of fluorolucent magnetic transmitting elements arranged in multiple layers. The fluorolucent magnetic transmitting elements can be those, as discussed in relation to FIG. 3C. Alternatively, or in addition, the magnetic transmitting array 90 can include magnetic transmitting elements, such as those discussed in relation to U.S. application Ser. No. 15/034,474, which is hereby incorporated by reference as though fully set forth herein. For example, the magnetic transmitting array 90 can include a first layer of magnetic transmitting elements, similar to those discussed in relation to FIG. 3. The first layer of magnetic transmitting elements can, for example, include a first magnetic transmitting element 92-1, a second magnetic transmitting element 92-2, a third magnetic transmitting element 92-3, a fourth magnetic transmitting element 92-4.

In some embodiments, each first layer magnetic transmitting element 92-1, 92-2, 92-3, 92-4 does not overlap one another. For example, each first layer magnetic transmitting element 92-1, 92-2, 92-3, 92-4 can be spaced apart from neighboring magnetic transmitting elements of the same layer. In some embodiments, the first layer magnetic transmitting elements 92-1, 92-2, 92-3, 92-4 can abut neighboring magnetic transmitting elements in the same layer. For example, the first magnetic transmitting element 92-1 of the first layer can abut the third magnetic transmitting element 92-3 of the first layer, but can be spaced apart from the second magnetic transmitting element 92-2 of the first layer. In some embodiments, the first layer magnetic transmitting elements 92-1, 92-2, 92-3, 92-4 can be arranged in a grid fashion, such that the central origin (e.g., central origins 93-1, 93-2, 93-3, 93-4) of each of the first layer magnetic transmitting elements 92-1, 92-2, 92-3, 92-4 forms a corner of a square, rectangle, rhombus, parallelogram, etc.

Further, the magnetic transmitting array 90 can include a second layer of magnetic transmitting elements 94-1, 94-2, 94-3, 94-4, a third layer of magnetic transmitting elements 96-1, 96-2, 96-3, 96-4, and a fourth layer of magnetic transmitting elements 98-1, 98-2, 98-3, 98-4. As discussed, the first layer, second layer, third layer, and fourth layer magnetic transmitting elements can be fluorolucent magnetic transmitting elements, such as those discussed with respect to FIG. 3C. The magnetic transmitting elements in the second layer, third layer, and/or fourth layer can be arranged in a spatial relationship similar to that discussed in relation to how the first layer magnetic transmitting elements 92-1, 92-2, 92-3, 92-4 are arranged, as described herein.

In some embodiments (not shown), the magnetic transmitting elements in the second layer, third layer, and/or fourth layer can be arranged in a different spatial relationship than the first layer magnetic transmitting elements 92-1, 92-2, 92-3, 92-4. For example, the first layer magnetic transmitting elements 92-1, 92-2, 92-3, 92-4 can be arranged such that one or more other layers (e.g., second layer, third layer, fourth layer) are arranged in a spatial relationship that is different than the first layer magnetic transmitting elements 92-1, 92-2, 92-3, 92-4. For example, the second layer magnetic transmitting elements 94-1, 94-2, 94-3, 94-4 can be arranged such that the central origin of each of the second layer magnetic transmitting elements 94-1, 94-2, 94-3, 94-4 forms a corner of a rectangle, while the first layer magnetic transmitting elements 92-1, 92-2, 92-3, 92-4 are arranged such that the central origin of each of the first layer magnetic transmitting elements 92-1, 92-2, 92-3, 92-4 forms a corner of a square. Thus, each of the first, second, third, and fourth layers of magnetic transmitting elements can be arranged in the same spatial relationship as the first layer magnetic transmitting elements 92-1, 92-2, 92-3, 92-4 or in a different spatial relationship than the first layer magnetic transmitting elements 92-1, 92-2, 92-3, 92-4.

Although four magnetic transmitting elements are depicted in each layer of the magnetic transmitting array 90, more than four magnetic transmitting elements or fewer than four magnetic transmitting elements can be included in each layer of the magnetic transmitting array 90. In some embodiments, magnetic transmitting elements in a range of from 1 to 20 can be included in each layer of the magnetic transmitting array 90. In some embodiments, the number of magnetic transmitting elements included in each respective layer of the magnetic transmitting array 90 can be in a range from 2 to 15. In some embodiments, the number of magnetic transmitting elements included in each respective layer of the magnetic transmitting array 90 can be in a range from 3 to 10. In some embodiments, the number of magnetic transmitting elements included in each respective layer of the magnetic transmitting array 90 can be in a range from 4 to 7. Further, although four layers of magnetic transmitting elements are depicted in the magnetic transmitting array 90, more than four layers of magnetic transmitting elements or fewer than four layers of magnetic transmitting elements can be included in the magnetic transmitting array 90. Some embodiments of the present disclosure can include from 1 to 8 layers of magnetic transmitting elements in the magnetic transmitting array 90. Some embodiments of the present disclosure can include from 2 to 5 layers of magnetic transmitting elements in the magnetic transmitting array 90.

In some embodiments, each magnetic transmitting element in the second, third, and fourth layer do not overlap magnetic transmitting elements within each respective layer, similar to first layer magnetic transmitting elements 92-1, 92-2, 92-3, 92-4. For example, the second layer magnetic transmitting elements 94-1, 94-2, 94-3, 94-4 do not overlap one another, nor do the magnetic transmitting elements in the third layer and fourth layer overlap one another. In some embodiments, magnetic transmitting elements in each respective layer do not overlap to prevent a short from occurring between each magnetic transmitting element in the layer.

In some embodiments, the first layer, second layer, third layer, and fourth layer magnetic transmitting elements can overlap magnetic transmitting elements in other layers. For example, as depicted, the second layer magnetic transmitting elements 94-1, 94-2, 94-3, 94-4 can overlap (e.g., partially overlap) the first layer magnetic transmitting elements 92-1, 92-2, 92-3, 92-4; the third layer magnetic transmitting elements 96-1, 96-2, 96-3, 96-4 can overlap the first layer magnetic transmitting elements 92-1, 92-2, 92-3, 92-4 and the second layer magnetic transmitting elements 94-1, 94-2, 94-3, 94-4; and the fourth layer magnetic transmitting elements 98-1, 98-2, 98-3, 98-4 can overlap the first layer magnetic transmitting elements 92-1, 92-2, 92-3, 92-4; the second layer magnetic transmitting elements 94-1, 94-2, 94-3, 94-4; and the third layer magnetic transmitting elements 96-1, 96-2, 96-3, 96-4.

Figure 4C:
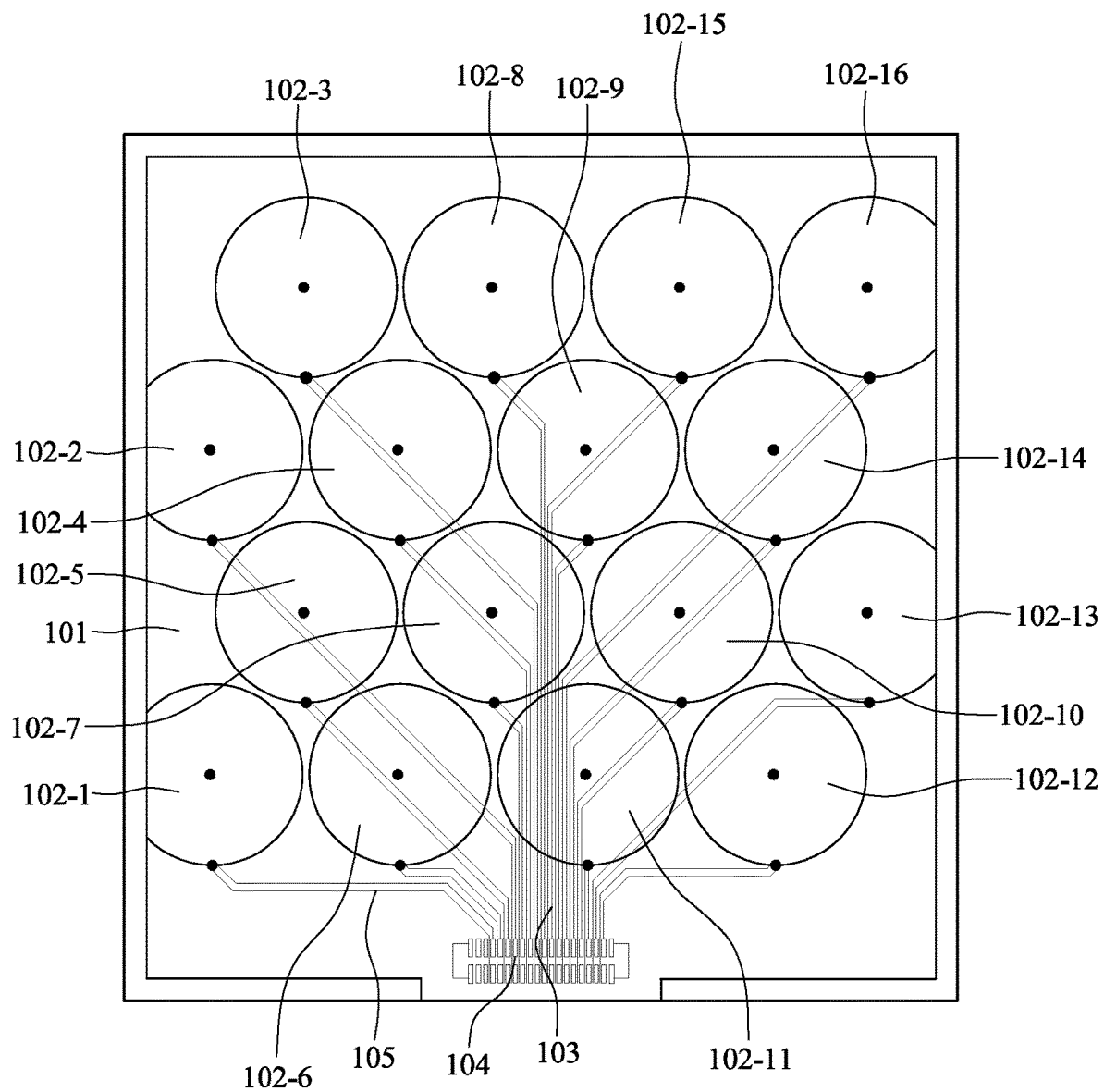
FIG. 4C depicts a top view of a first layer of magnetic transmitting elements of a magnetic transmitting array, in accordance with embodiments of the present disclosure.

Regardless of whether the magnetic transmitting element layers overlap, the layers may be arranged such that the magnetic transmitting elements are organized in a hexagonal lattice pattern or structure when viewed from a direction perpendicular to a plane in which the elements of a layer lie (as illustrated in FIGS. 4A and 4C). In such embodiments, the central origins of the transmitting elements can be considered to align with the vertices of the lattice. In embodiments where there is overlap between magnetic transmitting elements in different layers, the relative placement of the magnetic transmitting elements between layers may be optimized such that they are spread as much as possible within a constrained area (e.g., to concentrate a magnetic field in a volumetric area of interest such as a patient's body or, more specifically, the area around and/or in a patient's heart, for example), while at the same time minimizing the amount of obstruction produced in a fluoroscopic image where X-rays are passing through the magnetic transmitting element layers. In such embodiments, the hexagonal lattice structure can be analogized to a "beehive" like structure with overlapping "cells" as shown in FIG. 4A. As seen there, the radius of a transmitting element may be calculated as the square root of 3 divided by 2 times the distance between vertices on the lattice (in other words, the radius of a transmitting element may be equal to the "height" of an equilateral triangle formed by three adjacent vertices on the lattice).

In more detail and with continued attention to FIG. 4A, the second layer of magnetic transmitting elements 94-1, 94-2, 94-3, 94-4 can be arranged in a same spatial relationship as the first layer magnetic transmitting elements 92-1, 92-2, 92-3, 92-4 and the central origins (e.g., central origins 95-1, 95-2, 95-3, 95-4) of each of the second layer magnetic transmitting elements 94-1, 94-2, 94-3, 94-4 can be shifted in a first direction from the central origins (e.g., central origins 93-1, 93-2, 93-3, 93-4) of the first layer magnetic transmitting elements 92-1, 92-2, 92-3, 92-4. For example, as depicted, the central origins of each of the second layer magnetic transmitting elements 94-1, 94-2, 94-3, 94-4 can be shifted laterally in the first direction (e.g., to the right, with respect to the page) from the central origins of the first layer magnetic transmitting elements 92-1, 92-2, 92-3, 92-4.

In some embodiments, the third layer magnetic transmitting elements 96-1, 96-2, 96-3, 96-4 can be shifted laterally and vertically with respect to the first layer magnetic transmitting elements 92-1, 92-2, 92-3, 92-4. As depicted, the central origins (e.g., central origins 97-1, 97-2, 97-3, 97-4) of the third layer magnetic transmitting elements 96-1, 96-2, 96-3, 96-4 can be shifted between the central origins of the first layer magnetic transmitting elements 92-1, 92-2, 92-3, 92-4 and the second layer magnetic transmitting elements 94-1, 94-2, 94-3, 94-4. In an example, the central origins of the third layer magnetic transmitting elements 96-1, 96-2, 96-3, 96-4 can be shifted to the right (with respect to the page) of the central origins of the first layer magnetic transmitting elements 92-1, 92-2, 92-3, 92-4 by a smaller amount than the central origins of the second layer magnetic transmitting elements 94-1, 94-2, 94-3, 94-4.

In addition the central origins of the third layer magnetic transmitting elements 96-1, 96-2, 96-3, 96-4 can be shifted vertically (e.g., upward) with respect to the central origins of the first layer magnetic transmitting elements 92-1, 92-2, 92-3, 92-4. In some embodiments, the fourth layer magnetic transmitting elements 98-1, 98-2, 98-3, 98-4 can be shifted laterally with respect to the central origins of the first layer magnetic transmitting elements 92-1, 92-2, 92-3, 92-4, second layer magnetic transmitting elements 94-1, 94-2, 94-3, 94-4, and third layer magnetic transmitting elements 96-1, 96-2, 96-3, 96-4. For example, the central origins of the fourth layer magnetic transmitting elements 98-1, 98-2, 98-3, 98-4 can be shifted to the right of the central origins of the first layer, second layer, and third layer magnetic transmitting elements.

In addition, the central origins of the fourth layer magnetic transmitting elements 98-1, 98-2, 98-3, 98-4 can be shifted vertically (e.g., upward) from the central origins of the first layer magnetic transmitting elements 92-1, 92-2, 92-3, 92-4. For example, the central origins (e.g., central origins 99-1, 99-2, 99-3, 99-4) of the fourth layer magnetic transmitting elements 98-1, 98-2, 98-3, 98-4 can be shifted vertically from the first layer magnetic transmitting elements 92-1, 92-2, 92-3, 92-4 a same amount as the origins of the third layer magnetic transmitting elements 96-1, 96-2, 96-3, 96-4. As such, the overlapping magnetic transmitting elements can be arranged such that no through holes exist between the magnetic transmitting array 90, as depicted in FIG. 4A. For example, as depicted, the third layer magnetic transmitting element 96-3 covers a through hole that would exist between the first layer magnetic transmitting elements 92-1, 92-3 and second layer magnetic transmitting elements 94-1, 94-3.

To compensate for a low number of layers (e.g., two layers) of substrate forming the magnetic transmitting elements, the magnetic transmitting array 90 of the present disclosure can include layers of magnetic transmitting elements (e.g., as discussed in relation to FIG. 3) that overlap one another. For example, the first layer is overlapped by the second layer, which is overlapped by the third layer, which is overlapped by the fourth layer. A spacing between central origins of each magnetic transmitting element between neighboring layers can be approximately a radius between each coil. A separation between the central origins can be required so that a condition of the inverse solution to determine coil location is well determined. For example, the central origins of the first layer magnetic transmitting elements 92-1, 92-2, 92-3, 92-4 (e.g., central origins 93-1, 93-2, 93-3, 93-4) and adjacent second layer magnetic transmitting elements 94-1, 94-2, 94-3, 94-4 (e.g., central origins 95-1, 95-2, 95-3, 95-4) can be separated by a distance equivalent to a radius of one of the magnetic transmitting elements in the magnetic transmitting array 90. For instance, the first layer magnetic transmitting element 92-1 can be separated from neighboring second layer magnetic transmitting element 94-1 by a distance equivalent to a radius of one of the magnetic transmitting elements.

In some embodiments, the spacing between central origins of each magnetic transmitting element between neighboring layers can be greater than the radius between each coil. In some embodiments, the spacing between central origins of each magnetic transmitting element between neighboring layers can be less than the radius between each coil to create a more dense magnetic field.

As discussed herein, a central origin to central origin spacing of neighboring magnetic transmitting elements can be equivalent to or greater than a radius of one of the magnetic transmitting elements. Compared to a square array of square magnetic transmitting elements that does not overlap and that is of the same characteristic size, each magnetic transmitting element can enclose 40 percent more area, which when etched into an 11 centimeter diameter spiral with 1.8 mm pitch results in 95 percent more field per layer at the same current used in a square array of magnetic transmitting elements.

For the same dimensions, the trace length associated with the larger, overlapped spirals is only 10 percent longer than a trace length for a square shaped coil. For a given field strength, the result is that the larger overlapped spirals dissipate less than 30 percent of the heat compared to the square array of magnetic transmitting elements. Given the ability to use much thicker aluminum layers than copper without obscuring the fluoroscopic image, the resistance per layer can be reduced accordingly, resulting in an x-ray transparent transmitter array that is approximately an order of magnitude more efficient at generating an AC magnetic field than the square array of prior approaches.

As previously discussed, the overlapping magnetic transmitting elements can be arranged such that no through holes exist between the magnetic transmitting array 90, as depicted in FIG. 4A. For example, as depicted, the third layer magnetic transmitting element 96-3 covers a through hole that would exist between the first layer magnetic transmitting elements 92-1, 92-3 and second layer magnetic transmitting elements 94-1, 94-3. This can create a more dense magnetic field in some embodiments.

In some embodiments, the magnetic transmitting array 90 can be a fluorolucent magnetic transmitting array 90. For example, fluorolucent magnetic transmitting elements, such as those discussed in relation to FIG. 3C, can be included in the array 90. This can allow for the magnetic transmitting array 90 to be placed in a fluoro window 91, which can be a window through which x-rays from a fluoroscope pass. The fluorolucent nature of the magnetic transmitting array 90 can allow for x-rays to pass through the fluoro window 91 and the array 90, thus providing a fluoroscopic image that is unobstructed by the magnetic transmitting array 90.

FIG. 4B depicts a side view of an insulation layer 100 disposed between a first layer of magnetic transmitting elements and a second layer of transmitting elements, in accordance with embodiments of the present disclosure. In some embodiments an insulative layer can be disposed between one or more layers of the magnetic transmitting elements to prevent the magnetic transmitting elements from contacting one another. As depicted, the insulative layer 100 is disposed between first layer magnetic transmitting elements 92-3, 92-4 and second layer magnetic transmitting elements 94-3, 94-4. The insulative layer 100 can be disposed between the first layer magnetic transmitting elements 92-1, 92-2, 92-3, 92-4 and the second layer transmitting elements 94-1, 94-2, 94-3, 94-4; between the second layer magnetic transmitting elements 94-1, 94-2, 94-3, 94-4 and the third layer transmitting elements 96-1, 96-2, 96-3, 96-4; and/or between the third layer magnetic transmitting elements 96-1, 96-2, 96-3, 96-4 and the fourth layer transmitting elements 98-1, 98-2, 98-3, 98-4.

FIG. 4C depicts a top view of a first layer of magnetic transmitting elements 102-1, 102-2, . . . , 102-16 of a magnetic transmitting array, in accordance with embodiments of the present disclosure. The magnetic transmitting elements 102-1, 102-2, . . . , 102-16 can be fluorolucent, in some embodiments, such as the fluorolucent magnetic transmitting element discussed in relation to FIG. 3C. In an example, the first layer magnetic transmitting elements 102-1, 102-2, . . . , 102-16 can be arranged in a manner similar to how the first layer magnetic transmitting elements 92-1, 92-2, 92-3, 92-4 are arranged in FIG. 4A. For example, the first layer magnetic transmitting elements 102-1, 102-2, . . . , 102-16 can be arranged in a first plane, forming a first magnetic assembly layer. The first layer magnetic transmitting elements 102-1, 102-2, . . . , 102-16 do not overlap one another on the first plane, as depicted in FIG. 4C.

In some embodiments, a connection lead tree 103 can electrically couple each one of the first layer magnetic transmitting elements 102-1, 102-2, . . . , 102-16 to a connection pad 104, via individual connection leads (e.g., connection lead 105). The connection pad 104 can be connected to a plurality of connection leads, each of which is electrically coupled with one of the first layer magnetic transmitting elements 102-1, 102-2, . . . , 102-16. With reference to connection lead 105, the connection lead 105 electrically couples the first layer magnetic transmitting element 102-1 to the connection pad 104. Each of the magnetic transmitting elements 102-1, 102-2, . . . , 102-16 can be electrically coupled to the connection pad via terminals located at an outer edge of the magnetic transmitting element, as depicted in FIG. 4C and previously discussed in relation to FIG. 3C.

In some embodiments, the first layer magnetic transmitting elements 102-1, 102-2, . . . , 102-16, the lead tree 103, and/or the connection leads can be disposed on a substrate 101. In an example, the substrate can be rigid and/or flexible. In some embodiments, the substrate can be a printed circuit board on which the first layer magnetic transmitting elements 102-1, 102-2, . . . , 102-16 are disposed. In some embodiments, multiple layers of magnetic transmitting elements can be stacked on top of one another, as further described in relation to FIG. 4A. For example, one or more other layers of magnetic transmitting elements can be stacked on top of the first layer magnetic transmitting elements 102-1, 102-2, . . . , 102-16 and can be longitudinally or laterally offset from the first layer magnetic transmitting elements, as depicted and discussed in relation to FIG. 4A. In some embodiments, between 2 and 10 layers of magnetic transmitting elements can be stacked on top of one another. In some embodiments, by stacking multiple layers of magnetic transmitting elements on top of one another, a lateral width of the magnetic transmitting array can be reduced, enabling the magnetic transmitting array to fit within a fluoro window. However, in some embodiments, a single layer of magnetic transmitting elements can be used in the magnetic transmitting array.

Figure 5A:
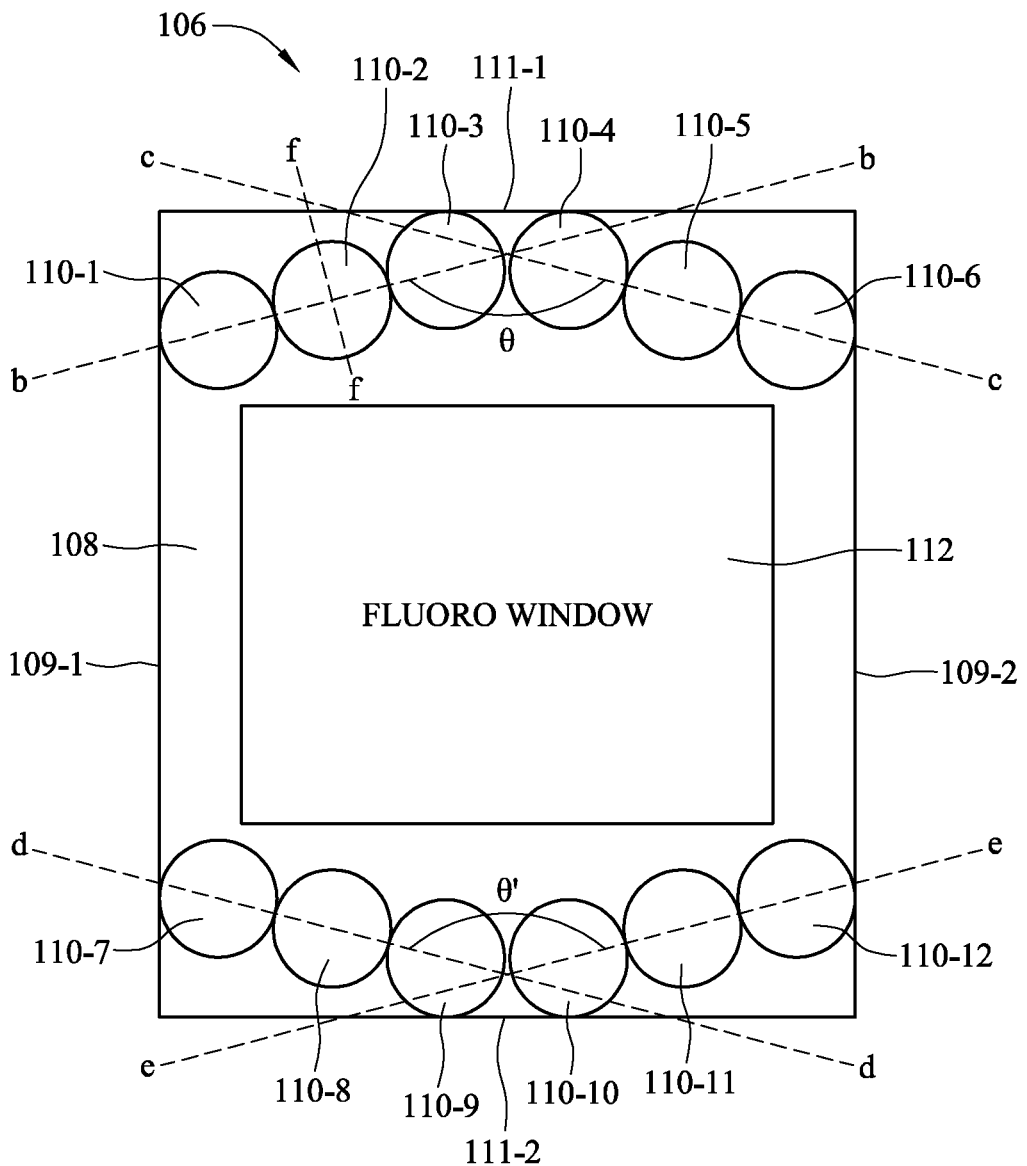
FIG. 5A depicts a diagrammatic top view of a second embodiment of a magnetic transmitting assembly, in accordance with embodiments of the present disclosure.

FIG. 5A depicts a diagrammatic a top view of a second embodiment of a magnetic transmitting assembly 106, in accordance with embodiments of the present disclosure. In some embodiments, the magnetic transmitting assembly 106 can include a frame 108 to which a plurality of electromagnetic transmitting elements 110-1, 110-2, . . . 110-12 can be disposed on. The frame 108 can be formed from a fluorolucent and/or radiopaque material in some embodiments. The frame 108 can be an enclosure, in some embodiments, as discussed in relation to FIG. 5B. The frame 108 can include a fluoro window 112 that can allow for x-rays to pass through a center of the frame 108 undisturbed by the frame 108 and/or by the magnetic transmitting elements 110-1, 110-2, . . . 110-12, thus allowing for an undisturbed fluoroscopy image. In some embodiments, the fluoro window 112 can be a square, as depicted. However, the fluoro window 112 can be any shape including a circle, square, triangle, etc.

In some embodiments, since the x-rays can pass through the fluoro window 112, the frame 108 can be formed from a radiopaque material because that portion of the magnetic transmitting assembly 106 will be outside of the fluoro window 112 and will not be visible in the fluoroscopy image. In some embodiments, the frame 108 can be formed of a non-metallic material (e.g., fiberglass). In some embodiments, the fluoro window 112 can be a cutout of the frame 108, as discussed herein. Alternatively, the fluoro window 112 can be formed from a material that is translucent or transparent in the fluoroscopy image.

In some embodiments, the plurality of electromagnetic transmitting elements 110-1, 110-2, . . . 110-12 can be equidistant from a center of the fluoro window 112 or as close to equidistant from the center of the fluoro window 112, as allowed by design. The plurality of electromagnetic transmitting elements 110-1, 110-2, . . . 110-12 can be flat copper coils and can be formed from a printed circuit board fabrication process. In an example, the electromagnetic transmitting elements 110-1, 110-2, . . . 110-12 can be non-fluorolucent. Each of the plurality of electromagnetic transmitting elements 110-1, 110-2, . . . 110-12 can allow for a plurality of layers of windings to be formed on each of the electromagnetic transmitting elements 110-1, 110-2, . . . 110-12. In an example, each of the plurality of electromagnetic transmitting elements 110-1, 110-2, . . . 110-12 can have up to 32 layers of windings. However, in some embodiments, additional layers of windings can be provided (e.g., 64 layers of windings, 128 layers of windings, hundreds of layers of windings).

The plurality of electromagnetic transmitting elements 110-1, 110-2, . . . 110-12 can be disposed on an upper portion 111-1 of the frame 108 and a lower portion 111-2 of the frame 108, with respect to the page, in some embodiments. Additionally, the electromagnetic transmitting elements 110-1, 110-2, . . . 110-12 can be disposed on a left side 109-1 of the frame 108 and a right side 109-2 of the frame 108, with respect to the page, although not shown. In some embodiments, when the electromagnetic transmitting elements 110-1, 110-2, . . . 110-12 are disposed on the lower portion of the frame 108 and the upper portion of the frame 108, the upper portion of the frame 108 and the lower portion of the frame 108 can be wider than the side portions of the frame that connect the upper portion and the lower portion. In some embodiments (not shown), the magnetic transmitting elements 110-1, 110-2, . . . 110-12 can be arranged in an upper arc-like segment and a lower arc-like segment. In some embodiments, each arc-like segment can be equidistant from a center of the fluoro window. As such, each of the magnetic transmitting elements 110-1, 110-2, . . . 110-12 can remain equidistant from the center of the fluoro window 112.

In some embodiments, as depicted, the upper set of magnetic transmitting elements 110-1, 110-2, . . . 110-6 can be arranged in a v-shape and the lower set of magnetic transmitting elements 110-7, 110-8, . . . 110-12 can be arranged in a v-shape, as shown. In an example, the upper set of magnetic transmitting elements 110-1, 110-2, . . . 110-6 can be disposed along lines bb and cc. For instance, the magnetic transmitting elements 110-1, 110-2, 110-3 can be disposed along the line bb and the magnetic transmitting elements 110-4, 110-5, 110-6 can be disposed along the line cc.

The lower set of magnetic transmitting elements 110-7, 110-8, . . . 110-12 can be disposed along lines dd and ee. For instance, the magnetic transmitting elements 110-7, 110-8, 110-9 can be disposed along the line dd and the magnetic transmitting elements 110-10, 110-11, 110-12 can be disposed along the line ee. Although the upper set of magnetic transmitting elements 110-1, 110-2, . . . 110-6 is shown as including six magnetic transmitting elements and the lower set of magnetic transmitting elements 110-7, 110-8, . . . 110-12 is shown as including six magnetic transmitting elements, each set of magnetic transmitting elements can include more than six magnetic transmitting elements or less than six magnetic transmitting elements. In some embodiments, each set of magnetic transmitting elements can include from 3 to 8 magnetic transmitting elements.

The lines bb and cc and lines dd and ee can be disposed at angles with respect to one another such that magnetic transmitting elements 110-1, 110-2, . . . 110-112 surround or partially surround the fluoro window 112. For example, the lines bb and cc can be disposed at an angle θ with respect to one another and the lines dd and ee can be disposed at an angle θ' with respect to one another. In some embodiments, the angles θ and θ' can be the same. In some embodiments, the angles θ and θ' can be in a range from 90 to 180 degrees. Because the magnetic transmitting elements 110-1, 110-2, . . . 110-12 surround or partially surround the fluoro window 112, a more uniform magnetic field is produced within the fluoro window 112 and areas that are located above the fluoro window 112 (e.g., area of interest 38 where a patient's chest may be located), allowing for a more uniform magnetic field for use with position sensors 28 (e.g., magnetic sensors) that are placed within the fluoro window 112.

One or more fluorolucent magnetic transmitting elements can be disposed between the magnetic transmitting elements 110-1, 110-2, . . . 110-12 within the fluoro window 112. In some embodiments, a magnetic transmitting array, as discussed in relation to FIG. 4A, can be disposed between the magnetic transmitting elements 110-1, 110-2, . . . 110-12 within the fluoro window 112. As discussed herein, the magnetic transmitting assembly 106 can supplement a magnetic field produced by the magnetic transmitting elements 110-1, 110-2, . . . 110-12. Alternatively, a different arrangement of fluorolucent magnetic transmitting elements, as discussed in relation to FIG. 3D can be placed in the fluoro window 112. For example, an arrangement of fluorolucent magnetic transmitting elements, as discussed in relation to FIG. 6, can be placed in the fluoro window 112.

Figure 5B:
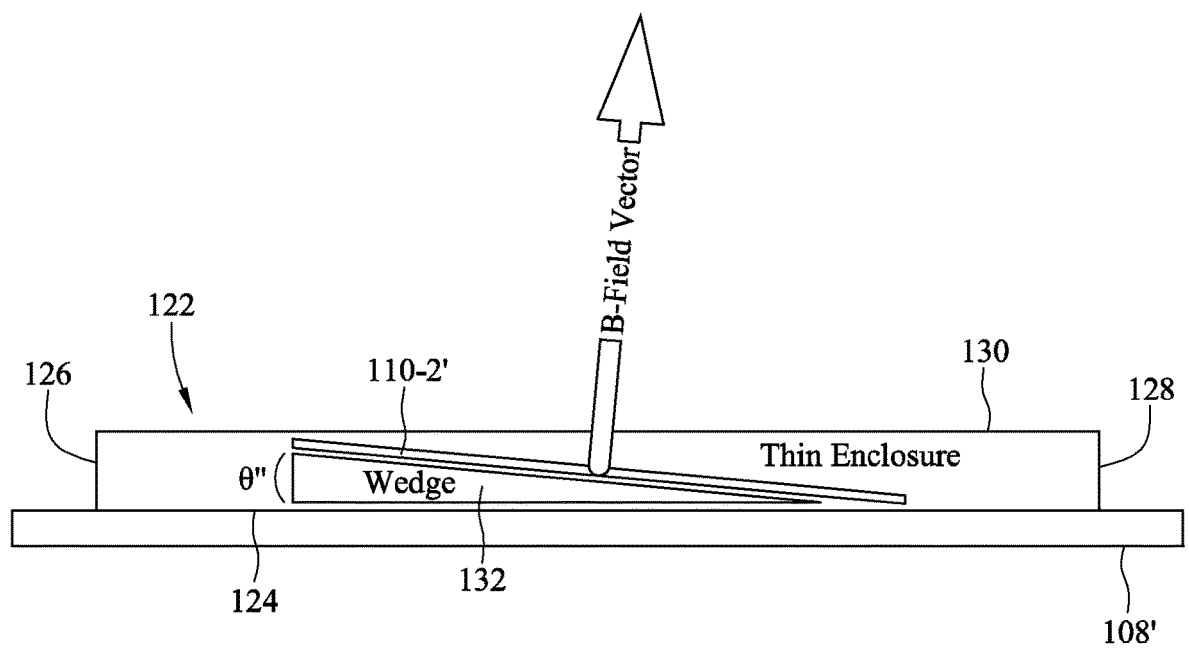
FIG. 5B is a cross-sectional view along line ff of a magnetic transmitting element in an enclosure, which can be included in the magnetic transmitting assembly in FIG. 5A, in accordance with embodiments of the present disclosure.

FIG. 5B is a diagrammatic cross-sectional view along line ff of a magnetic transmitting element 110-2' in an enclosure 122, which can be included in the magnetic transmitting assembly 106 in FIG. 5A, in accordance with embodiments of the present disclosure. Although the above discussion is with respect to magnetic transmitting element 110-2', the following discussion applies to all of the magnetic transmitting elements 110-1, 110-2, . . . 110-12 (also referred to herein as magnetic transmitting elements 110) discussed in relation to FIG. 5A. In some embodiments, one or more of the magnetic transmitting elements 110 can be housed inside of one or more enclosures 122. For example, the magnetic transmitting element 110-2' can be housed in the enclosure 122. In an example, each magnetic transmitting element 110 can be housed inside of an individual enclosure. In some embodiments, multiple magnetic transmitting elements 110 can be housed inside of an enclosure. The enclosure 122 can include a base 124 to which the magnetic transmitting element 110 is mounted. In some embodiments, the enclosure can be mounted on the frame 108'. The enclosure 122 can include outer walls 126, 128 that extend vertically from the base 124 and are connected to a top 130, which serves to enclose the magnetic transmitting element 110-2'. The base 124 of the enclosure can be in a shape of a square, rectangle, triangle, circle, etc. and can be formed from a material such as, for example, fiberglass. In some embodiments, the top 130 can be the same shape as the base.

In some embodiments, a wedge 132 can be placed under the magnetic transmitting element 110-2' to cause the magnetic transmitting element 110-2' to be disposed at an angle. In some embodiments, the magnetic transmitting element 110-2' can be disposed at an angle $\theta''$ in a range from 1 to 20 degrees, 2 to 10 degrees, or 3 to 7 degrees; although the magnetic transmitting element 110-2' can be disposed at an angle that is less than 1 degree or greater than 20 degrees in some embodiments. In an example, the angle at which the magnetic transmitting element 110-2' is disposed can be limited by a desired thickness of the magnetic transmitting assembly 106. For example, the magnetic transmitting assembly 106 can be placed underneath a mattress associated with a patient examination table. If the angle at which the magnetic transmitting elements 110-2' are disposed is too great, a thickness of the magnetic transmitting assembly 106 can be such that it may protrude from the patient examination table by an amount that causes it to be noticeable to a patient and cause discomfort.

In some embodiments, each of the magnetic transmitting elements 110 can be disposed at an angle with respect to the base 124. For example, as discussed herein, the magnetic transmitting element 110-2' can be disposed at an angle $\theta''$ via the wedge 132. In some embodiments, all of the magnetic transmitting elements (e.g., 110-1, 110-2, . . . 110-12) can be disposed at the angle $\theta''$. While each of the magnetic transmitting elements 110 can be disposed at the same angle $\theta''$, each magnetic transmitting element 110 can have a different directionality. For example, each magnetic transmitting element 110 can be disposed at the same angle $\theta''$ around the fluoro window 112, such that a magnetic field vector (e.g., B-field vector) produced by each of the magnetic transmitting elements 110 is directed toward the fluoro window 112. For instance, each of the magnetic transmitting elements 110 can be disposed at the same angle $\theta''$, such that the magnetic field vector produced by each of the magnetic transmitting elements 110 is directed toward a common point located in the area of interest 38. In some embodiments, each of the magnetic transmitting elements 110 can be disposed at the same angle $\theta''$, such that the magnetic field vector produced by each of the magnetic transmitting elements 110 is directed toward a common point located in the area of interest 38 (FIG. 2). In either case, the magnetic transmitting elements 110 should be directed in a way that causes a magnetic field to be formed in the area of interest 38.

In some embodiments, the angle $\theta''$ can be perpendicular to the line bb depicted in FIG. 5A. For example, the magnetic transmitting elements 110-1, 110-2, 110-3 can be disposed at the same angle $\theta''$ and with a same directionality. In some embodiments, the magnetic transmitting elements 110-4, 110-5, 110-6 can be disposed at the same angle $\theta''$, but with a different directionality as opposed to magnetic transmitting elements 110-1, 110-2, 110-3. For example, the angle $\theta''$ at which each of the magnetic transmitting elements 110-4, 110-5, 110-6 is disposed can be perpendicular to the line cc depicted in FIG. 5A. In some embodiments, the magnetic transmitting elements 110-7, 110-8, 110-9 can be disposed at the same angle $\theta''$, but with a different directionality as opposed to magnetic transmitting elements 110-1, 110-2, 110-3 and magnetic transmitting elements 110-4, 110-5, 110-6. For example, the angle $\theta''$ at which each of the magnetic transmitting elements 110-7, 110-7, 110-9 is disposed can be perpendicular to the line dd depicted in FIG. 5A. In some embodiments, the magnetic transmitting elements 110-10, 110-11, 110-12 can be disposed at the same angle $\theta''$, but with a different directionality as opposed to magnetic transmitting elements 110-1, 110-2, 110-3, 110-4, 110-5, 110-6, 110-7, 110-7, and 110-9. For example, the angle $\theta''$ at which each of the magnetic transmitting elements 110-10, 110-11, 110-12 is disposed can be perpendicular to the line ee depicted in FIG. 5A.

Figure 5C:
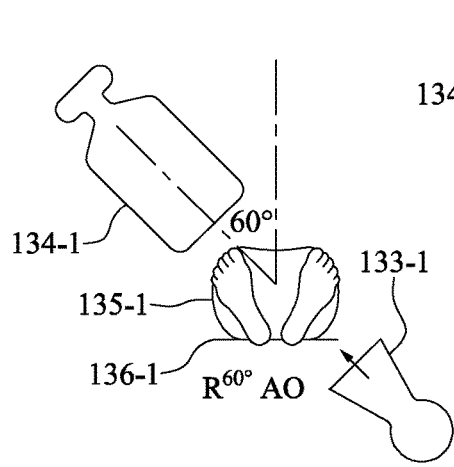
FIGS. 5C to 5H depict x-ray sources and x-ray image intensifiers at various positions with respect to a patient's body, in accordance with embodiments of the present disclosure.
Figure 5D:
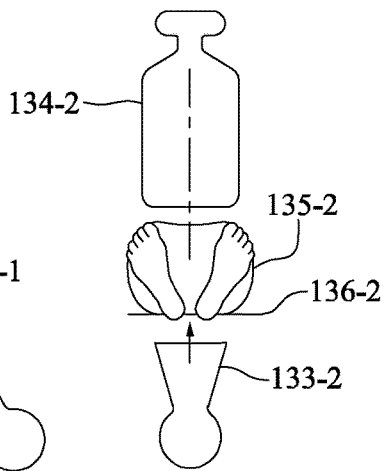
Figure 5E:
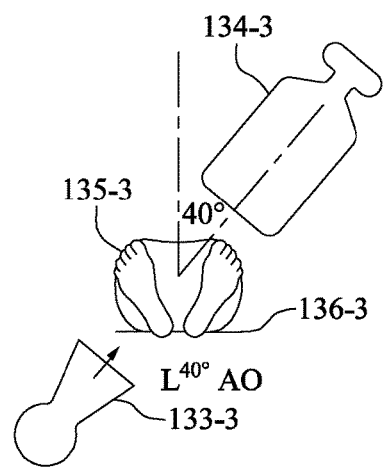
Figure 5F:
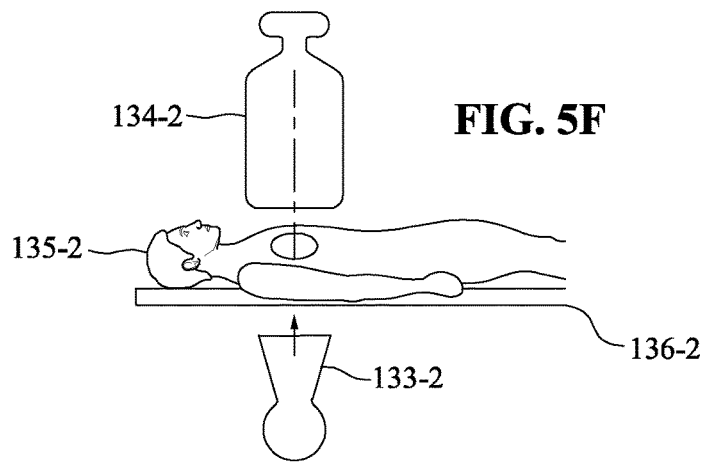
Figure 5G:
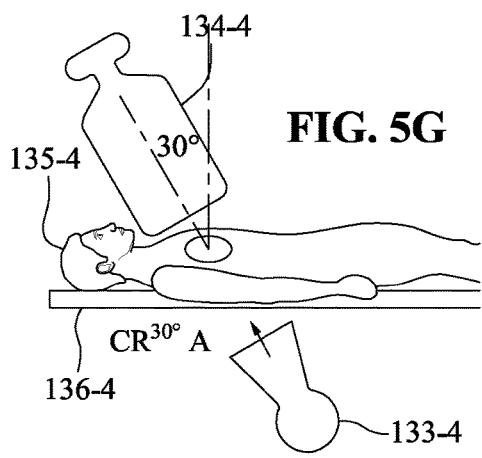
Figure 5H:
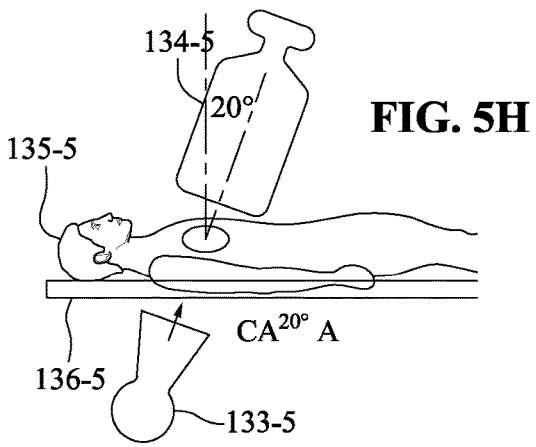

FIGS. 5C to 5H depict x-ray sources 133 and x-ray image intensifiers 134 at various positions with respect to a patient's body 135, in accordance with embodiments of the present disclosure. As depicted in FIG. 5C, an x-ray beam emitted from the x-ray source 133-1 is directed through a right anterior oblique 60 degree angle with respect to a line extending perpendicular from an examination table 136-1 on which the patient 135-1 is laying. As depicted in FIG. 5D and 5F, an x-ray beam emitted from the x-ray source 133-2 is directed at a 0 degree angle with respect to a line extending perpendicular from an examination table 136-2 on which the patient 135-2 is laying. As depicted in FIG. 5E, an x-ray beam emitted from the x-ray source 133-3 is directed at a left anterior oblique 40 degree angle with respect to a line extending perpendicular from an examination table 136-3 on which the patient 135-3 is laying. As depicted in FIG. 5G, an x-ray beam emitted from the x-ray source 133-4 is directed at a cranial 30 degree angle with respect to a line extending perpendicular from an examination table 136-4 on which the patient 135-4 is laying. As depicted in FIG. 5H, an x-ray beam emitted from the x-ray source 133-5 is directed at a caudal 20 degree angle with respect to a line extending perpendicular from an examination table 136-5 on which the patient 135-5 is laying.

With further reference to FIGS. 5A to 5H, in some embodiments, non-fluorolucent magnetic transmitting elements 110 may not be disposed on either side 109-1, 109-2 of the frame 108, depicted in FIG. 5A. In some embodiments, by excluding magnetic transmitting elements 110 from being disposed on either side 109-1, 109-2 of the frame 108, x-rays can pass through either side of the frame 108 when the x-ray source 133 and the image intensifier are disposed at angles similar to those depicted in FIGS. 5C and 5E. For example, because the x-ray source 133 is disposed at an angle in FIG. 5C and FIG. 5E, this can cause either side 109-1, 109-2 of the frame 108 to be disposed between the x-ray source 133 and the image intensifier 134. If non-fluorolucent magnetic transmitting elements were included on either side 109-1, 109-2 of the frame 108, a fluoroscopic image may be obstructed. In some embodiments, to account for the positioning of the x-ray source 133, fluorolucent magnetic transmitting elements, such as those discussed in relation to FIG. 3C can be disposed on either side of the frame 108.

In some embodiments, with further reference to FIGS. 5A to 5H, the magnetic transmitting elements 110 can be disposed in a pattern that is v-shaped, as depicted in FIG. 5A or along an arc-like segment (not depicted). By arranging the magnetic transmitting elements 110 in a v-shape or arc-like segment, the x-rays can pass through the frame 108 in between each arm of the v-shape (e.g., defined by lines bb and cc or lines dd and ee) or arc-like segment, when the x-ray source 133-4, 133-5 is disposed in positions depicted in FIGS. 5G and 5H. For example, when the x-ray source 133-4, 133-5 is disposed in positions depicted in FIGS. 5G and 5H, a portion of the frame 108 that is located in between each arm of the v-shape can be disposed between the x-ray source 133-4, 133-5 and each respective image intensifier 134-4, 134-5. This can allow for a fluoroscopic image that is unobstructed by the magnetic transmitting elements 110.

Figure 6:
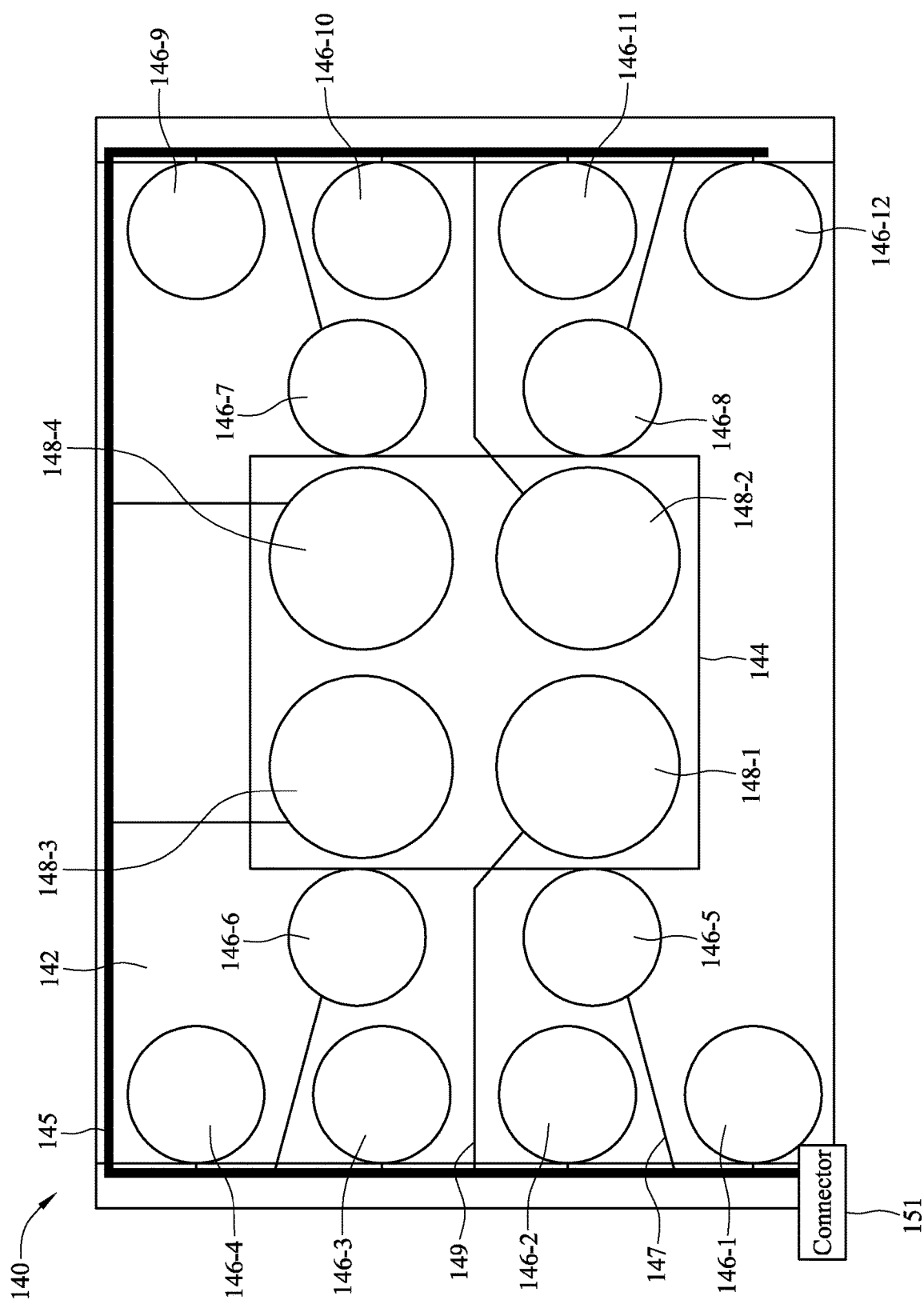
FIG. 6 depicts a top view of a third embodiment of a magnetic transmitting assembly, in accordance with embodiments of the present disclosure.

FIG. 6 depicts a top view of a third embodiment of a magnetic transmitting assembly 140, in accordance with embodiments of the present disclosure. The magnetic transmitting assembly 140 can include a frame 142, in some embodiments. The frame 142 can be formed from a fluorolucent and/or radiopaque material in some embodiments. The frame 142 can be an enclosure, in some embodiments, as discussed in relation to FIG. 5B. In some embodiments, the frame 142 can be a rectangle, as depicted, and the frame 142 can include a square cutout where the fluoro window 144 is located. Alternatively, instead of a cutout where the fluoro window 144 is located, the fluoro window can include a fluorolucent material that allows x-rays to pass through unobstructed.

In some embodiments, a plurality of electromagnetic transmitting elements 146-1, 146-2, . . . 146-12 can be disposed on the frame 142. The electromagnetic transmitting elements 146-1, 146-2, . . . 146-12 can be flat copper coils, in some embodiments, and can be disposed around the outside of the fluoro window 144 so they are not visible on an x-ray. As discussed in relation to FIG. 5A, the electromagnetic transmitting elements 146-1, 146-2, . . . 146-12 can be non-fluorolucent. Because the electromagnetic transmitting elements 146-1, 146-2, . . . 146-12 are disposed outside of the fluoro window, the fluoroscopy image can remain unobstructed by the electromagnetic transmitting elements 146-1, 146-2, . . . 146-12.

A first row of electromagnetic transmitting elements 146-5, 146-6 can be disposed on a first side of the fluoro window 144 and a second row of electromagnetic transmitting elements 146-7, 146-8 can be disposed on a second side of the fluoro window 144, opposite the first side. The first row of magnetic transmitting elements 146-5, 146-6 can be parallel with the second row of magnetic transmitting elements 146-7, 146-8 and spaced from a center of the fluoro window 144 a same distance as the second row of magnetic transmitting elements 146-7, 146-8. For example, corresponding magnetic transmitting elements in the first and second rows (e.g., magnetic transmitting element 146-6 and magnetic transmitting element 146-7) can be equally spaced from the center of the fluoro window 144.

In some embodiments, a third row of magnetic transmitting elements 146-1, 146-2, 146-3, 146-4 can be disposed on the first side of the fluoro window 144 and a fourth row of magnetic transmitting elements 146-9, 146-10, 146-11, 146-12 can be disposed on the second side of the fluoro window 144, opposite the first side. The third row of magnetic transmitting elements 146-1, 146-2, 146-3, 146-4 can be parallel with the fourth row of magnetic transmitting elements 146-9, 146-10, 146-11, 146-12 and spaced from a center of the fluoro window 144 a same distance as the fourth row of magnetic transmitting elements 146-9, 146-10, 146-11, 146-12. For example, corresponding magnetic transmitting elements in the third and fourth rows (e.g., magnetic transmitting element 146-3 and magnetic transmitting element 146-10) can be equally spaced from the center of the fluoro window 144.

In some embodiments, the first, second, third, and fourth rows of magnetic transmitting elements 146-1, 146-2, . . . 146-12 can be parallel with one another. In some embodiments, as depicted, the first, second, third, and fourth rows of magnetic transmitting elements 146-1, 146-2, . . . 146-12 can be parallel with an edge of the fluoro window 144 located on the first side and the second side.

In some embodiments, a spacing between magnetic transmitting elements in each of the first and second rows can be greater than a spacing between magnetic transmitting elements in each of the third and fourth rows. For example, a spacing between a central origin of each magnetic transmitting element 146-5, 146-6 in the first row can be greater than a spacing between a central origin of each magnetic transmitting element 146-1, 146-2, 146-3, 146-4 in the third row. In some embodiments, the spacing between the central origin of each magnetic transmitting element 146-5, 146-6 in the first row can be 1.25 to 2 times greater than the spacing between the central origin of each magnetic transmitting element 146-1, 146-2, 146-3, 146-4 in the third row. The ratio of spacing between central origins of the magnetic transmitting elements in the second and fourth rows can be the same or similar to the spacing between the central origins of the magnetic transmitting elements in the first and second rows.

In some embodiments, the spacing between the central origins of each magnetic transmitting element 146-1, 146-2 in the first row can be the same as the spacing between the central origins of each magnetic transmitting element 146-7, 146-8 in the second row. Further, the spacing between the central origins of each magnetic transmitting element 146-1, 146-2, 146-3, 146-4 in the third row can be the same as the spacing between the central origins of each magnetic transmitting element 146-9, 146-10, 146-11, 146-12 in the fourth row. The equal spacing between each of the magnetic transmitting elements can help produce a uniform magnetic field throughout the area of interest 38, in some embodiments. In some embodiments, spacing between the first and second row magnetic transmitting elements can be the same or similar and the spacing between the third and fourth row magnetic transmitting elements can be the same or similar to produce the uniform magnetic field. In some embodiments, the magnetic transmitting elements 146-1, 146-2, . . . 146-12 can be disposed at an angle, as discussed in relation to FIG. 5B to create field diversity.

In contrast to FIG. 5A, in some embodiments, fluorolucent magnetic transmitting elements can be disposed within the fluoro window 144. As depicted, four fluorolucent magnetic transmitting elements 148-1, 148-2, 148-3, 148-4 can be disposed in the fluoro window 144. In some embodiments, the fluorolucent magnetic transmitting elements 148-1, 148-2, 148-3, 148-4 can be similar to or the same as those depicted and discussed in relation to FIG. 3C. The fluorolucent magnetic transmitting elements 148-1, 148-2, 148-3, 148-4 can be disposed in a grid pattern, as depicted, with a central origin of each of the fluorolucent magnetic transmitting elements 148-1, 148-2, 148-3, 148-4 aligned with a corner of a square. The central origins of the fluorolucent magnetic transmitting elements 148-1, 148-2, 148-3, 148-4 can be arranged in other patterns, for example, a rectangle, triangle, etc. In some embodiments, the central origins of the fluorolucent magnetic transmitting elements can be equidistant from a center of the fluoro window 144.

In some embodiments, fewer than four fluorolucent magnetic transmitting elements can be disposed in the fluoro window 144 or more than four fluorolucent magnetic transmitting elements can be disposed in the fluoro window 144. In some embodiments, the number of fluorolucent magnetic transmitting elements disposed in the fluoro window 144 can be in a range from 1 to 12. In some embodiments, the number of fluorolucent magnetic transmitting elements disposed in the fluoro window 144 can be in a range from 3 to 10. In some embodiments, the magnetic transmitting assembly 90, as discussed in relation to FIG. 4A, can be disposed in the fluoro window 144. In some embodiments, the fluorolucent magnetic transmitting elements 148-1, 148-2, 148-3, 148-4 can be disposed on the same plane as that of the magnetic transmitting elements 146-1, 146-2, . . . 146-12.

In some embodiments, the spacing between a central origin of each magnetic transmitting element in the first row of magnetic transmitting elements 146-5, 146-6 (e.g., geometric centers of each of the magnetic transmitting elements 146-5, 146-6) can be the same as a spacing between a central origin of the fluorolucent magnetic transmitting elements 148-1, 148-3. In addition, the spacing between the central origin of the first row of magnetic transmitting elements 146-5, 146-6 and between the central origin of the fluorolucent magnetic transmitting elements 148-1, 148-3 can be the same as a spacing between a central origin of the second row of magnetic transmitting elements 146-5, 146-6 and between a central origin of the fluorolucent magnetic transmitting elements 148-2, 148-4. In some embodiments, a central origin of each of the magnetic transmitting elements 146-6, 146-7 and fluorolucent transmitting elements 148-3, 148-4 can be in line with one another, as depicted in FIG. 6. In some embodiments, a central origin of each of the magnetic transmitting elements 146-5, 146-8 and fluorolucent transmitting elements 148-1, 148-2 can be in line with one another, as depicted in FIG. 6.

In some embodiments, the fluoro window 144 can be formed from a fluorolucent material. In some embodiments, the fluorolucent material can be a polyimide. The fluorolucent material can prevent or reduce interference with a fluoroscopy image. In an example, the patient can be positioned on the patient examination table such that their heart is positioned above the fluoro window 144 in the area of interest 38 (FIG. 2). The magnetic field produced by the magnetic transmitting elements 146-1, 146-2, . . . 146-12 and fluorolucent magnetic transmitting elements 148-1, 148-2, 149-3, 148-4 can be used to provide a magnetic navigation field for use with position sensors 28 disposed within a catheter, in an example. In addition, fluoroscopic images of the heart can be captured with little to no interference caused by the fluorolucent material, which forms the fluoro window 144 or the fluorolucent magnetic transmitting elements.

In some embodiments, one or more twisted cabling 145 can provide power to each one of the magnetic transmitting elements 146-1, 146-2, . . . 146-12 or fluorolucent magnetic transmitting elements 148-1, 148-2, 148-3, 148-4. A plurality of leads 147, 149 can be connected to the one or more twisted cabling 145 to provide power to each one of the magnetic transmitting elements 146-1, 146-2, . . . 146-12 or fluorolucent magnetic transmitting elements 148-1, 148-2, 148-3, 148-4. Each lead 147, 149 can include one or more wires configured to provide power to a respective magnetic transmitting element 146-1, 146-2, . . . 146-12 or fluorolucent magnetic transmitting element 148-1, 148-2, 148-3, 148-4. For example, lead 147 can provide power to magnetic transmitting element 146-5 and lead 149 can provide power to fluorolucent transmitting element 148-1. As depicted, the other magnetic transmitting elements and fluorolucent magnetic transmitting elements can include their own respective leads that are configured to provide power.

In some embodiments, a power source and/or controller can be connected to a connector 151 to provide power to and/or control of the fluorolucent magnetic transmitting elements 148-1, 148-2, 148-3, 148-4 and/or magnetic transmitting elements 146-1, 146-2, . . . 146-12. In an example, the medical positioning system 14 (FIG. 1A) can be connected to the connector.

As discussed herein, multiple drive coils can be used instead of a single coil to create a magnetic transmitting array. As used herein, a drive coil can include a magnetic transmitting element, which can be fluorolucent and/or non-fluorolucent as discussed in relation to FIGS. 4, 5A, and 6. The magnetic transmitting element can be driven to create a magnetic field. In some embodiments, multiple drive coils can provide a sufficient spatially-unique and orientation-unique signal (e.g., excitation signal, magnetic field) at any point in 3D space where it is desired to determine the location and orientation of an electromagnetic position sensor. The unique signals can be created using a specific frequency to excite each drive coil, although time domain methods can alternatively be employed, which can transmit the same frequency at different time points. An electromagnetic position sensor amplifier and signal processor can measure a unique amplitude value attributable to each drive coil (in the case of frequency division multiplexing, synchronous demodulation for example, can be used).

In a system including multiple drive coils, it can be advantageous that excitation from one drive coil does not couple into adjacent drive coils and then re-radiate from those coils, as this may confound the subsequent means to derive accurate location of the sense coils. Assuming the method of exciting each coil with a unique frequency, the desired physical behavior which leads to the simplest mathematical model is that each frequency only represents emanation from a single drive coil at its (known apriori) location. Coupling and re-radiating from neighbor coils is undesirable.

Locating and orienting a sensing coil can require three degrees of freedom for the location, and two degrees of freedom for orientation (sometimes denoted pitch and yaw, and noting that the 'rotation' of a solenoidal sense coil is not solved for as it is symmetric). This can mean that a minimum of five drive coils can be required. More than five coils can be useful for solving for additional parameters such as system gain, or for extending the viable sensing region.

Multiple fluorolucent magnetic transmitting elements, as described herein, can be fairly easy to replicate and drive with unique frequencies. However, conventional solenoidal drive coils can have inductances in 10's of millihenries, and are typically paired with a series capacitor to create a tuned resonant circuit at the desired drive frequency for that particular coil. A side benefit of the conventional arrangement is that a resonant coil presents a higher impedance to other frequencies such as those used in adjacent coils. This can reduce its susceptibility to unwanted coupling of excitation signals from neighboring coils. In the case of the fluorolucent magnetic transmitting elements, as described herein, the inductance can be lower. For example, the fluorolucent magnetic transmitting element can have an inductance in a range from 0.1 to 4 millihenry. In some embodiments, the fluorolucent magnetic transmitting element can have an inductance of around 0.25 millihenries. Conventional drive coils driven with a resonant circuit can only be driven at the resonant frequency. Low inductance coils (e.g., fluorolucent magnetic transmitting elements) as described in the present disclosure can be driven at many different frequencies, simultaneously. This can allow for the same physical assembly (e.g., fluorolucent magnetic transmitting element) to simultaneously be driven with high frequencies to achieve a high signal to noise ratio while simultaneously being driven with low frequencies to characterize the environment. The low inductance coils, as described in embodiments of the present disclosure, also make manufacturing more robust because use of resonant circuits require capacitance matching. Capacitance matching can be uniquely done for each transmitter coil and can add time, cost, and variance to manufacturing. As low-inductance coils do not require resonant circuits, they also do not require capacitance matching, saving time and money while also resulting in tighter electrical tolerances.

Figure 7:
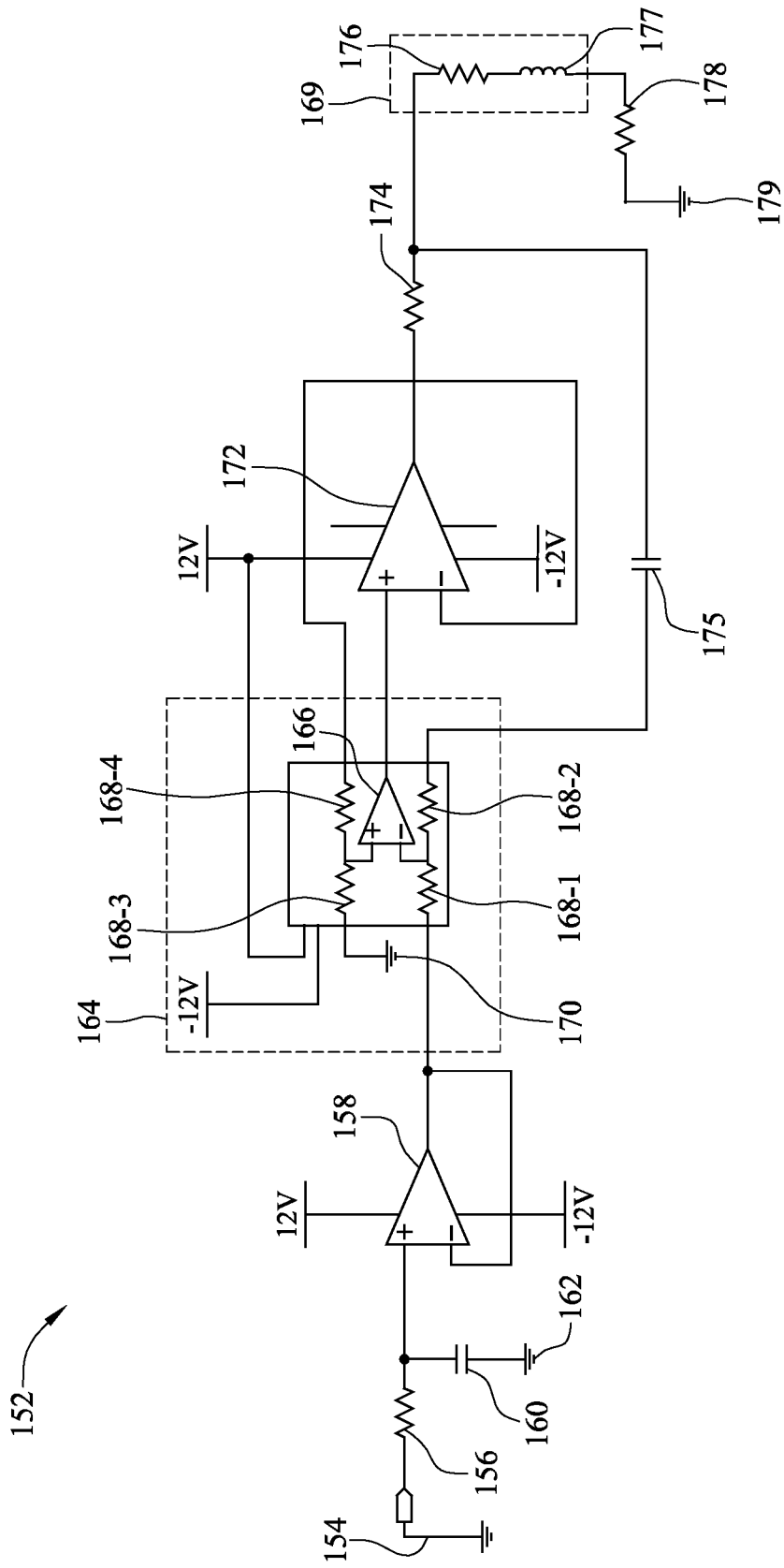
FIG. 7 depicts a schematic view of a first embodiment of a drive circuit for a fluorolucent magnetic transmitting element, in accordance with embodiments of the present disclosure.

FIG. 7 depicts a schematic view of a first embodiment of a drive circuit 152 for a fluorolucent magnetic transmitting element, in accordance with embodiments of the present disclosure. The drive circuit 152 can be a modified Howland drive circuit, in some embodiments. In some embodiments, the drive circuit 152 can be a high impedance drive circuit used for driving a fluorolucent magnetic transmitting element, such as that discussed in relation to FIG. 3C. As further discussed herein, where a plurality of fluorolucent magnetic transmitting elements are being driven, each fluorolucent magnetic transmitting element can be driven by a separate drive circuit 152. With reference to FIG. 7, an alternating current (e.g., sine waveform) can be supplied to the drive circuit 152 via an input 154 at a desired frequency. In some embodiments, the frequency can be in a range from 1 to 20 kilohertz in a sine waveform, although the frequency can be greater than 20 kilohertz or less than 1 kilohertz. The input 154 can be generated by a digital-to-analog converter in some embodiments (not shown). The input 154 can be provided to an input resistor 156 that is electrically connected to the input 154. The input resistor 156 can have a resistance of 1 kilohm, in some embodiments, although the resistor can have a resistance that is greater than or less than 1 kilohm. The input resistor 156 can be part of a low-pass smoothing filter along with an input capacitor 160. The input resistor 156 and the input capacitor 160 can be chosen together to form an RC low-pass filter to give a desired pole. Practically, the cutoff should be somewhere at least twice the frequency of the voltage input 154. In some embodiments, a cutoff frequency associated with the RC low-pass filter can be approximately twice the frequency of the input 154, but less than half of the digital-to-analog sampling rate. In some embodiments, an output of the input resistor 156 can be coupled (e.g., electrically coupled) to a non-inverting input of an input operational amplifier 158. A first capacitor can also be coupled to the output of the input resistor 156 to serve as a smoothing pole, in some embodiments. The smoothing pole can have a frequency in a range from 10 kilohertz to 60 kilohertz, in some embodiments. In an example, the smoothing pole can have a frequency of approximately 48 kilohertz. In some embodiments, the input capacitor 160 can be coupled to a ground 162.

In some embodiments, the input operational amplifier 158 can be configured for unity gain, acting as a buffer circuit. In some embodiments, the input operational amplifier 158 can be an AD823AR operational amplifier manufactured by Analog Devices, Inc. The output of the input operational amplifier 158 can be coupled to an inverting input of a Howland current source 164. The Howland current source 164 can include a first Howland resistor 168-1 coupled between the output of the first operational amplifier and an inverting input of a Howland operational amplifier 166 of the Howland current source 164. In some embodiments, the Howland current source can be an AD8276ARMZ operational amplifier manufactured by Analog Devices, Inc. Additionally, the Howland current source 164 can include a second Howland resistor 168-2 coupled in series with the first Howland resistor 168-1 and the inverting input of the Howland operational amplifier 166 of the Howland current source 164. The Howland current source 164 can include a non-inverting input coupled between a third Howland resistor 168-3 and a fourth Howland current resistor 168-4. The third Howland resistor 168-3 can be coupled to a second ground 170 and the fourth Howland resistor 168-4 can be coupled to an inverting input of an output operational amplifier 172.

The Howland resistors 168-1, 168-2, 168-3, 168-4 can be 40 kilohms and can be rated as trimmed to better than 0.02 percent matching. In some embodiments, an output of the Howland operational amplifier 166 of the Howland current source 164 can be coupled with a non-inverting input of the output operational amplifier 172, which is in a follow configuration to supply desired current levels. The output operational amplifier 172 can be an OPA548T operational amplifier manufactured by Texas Instruments.

In some embodiments, an output of the output operational amplifier 172 can be coupled with an output resistor 174. The output resistor 174 can have a resistance of 10 Ohms, in some embodiments. An output of the output resistor 174 can be coupled with a phase lead capacitor 175 and an output of the phase lead capacitor 175 can be coupled to the second Howland resistor 168-2. The output of the output resistor 174 can additionally be coupled with a fluorolucent magnetic transmitting element 169, as discussed herein, that includes a load represented by a resistance 176 and an inductance 177, in some embodiments. In an example, the resistance 176 can be 14.5 Ohms and the inductance 177 can be 1 millihenry. In some embodiments, the phase lead capacitor 175 can be selected to match (e.g., correspond with) an inductance 177 (e.g., inductance) of the fluorolucent magnetic transmitting element. For example, the phase lead capacitor 175 can have a capacitance of 10 nanofarads, which can match an inductance 177 of 1 millihenry. However, the capacitance of the phase lead capacitor 175 can vary with respect to the inductance 177 of the fluorolucent magnetic transmitting element. In some embodiments, where the fluorolucent magnetic transmitting element has an inductance 177 of 0.25 millihenry or less, a phase lead capacitor may not be needed.

In some embodiments, the fluorolucent magnetic transmitting element can have a resistance 176 that is greater than or less than 14.5 Ohms and an inductance 177 that is greater than or less than 1 millihenry. In some embodiments, the inductance 177 can be in a range of from 0.1 to 4 millihenry or in a range from 0.1 to 2 millihenry. The resistance 176 and the inductance 177 are illustrated as in series with the output of the output resistor 174, thus representing the load of the fluorolucent magnetic transmitting element. In some embodiments, a ballast 178 can be coupled between the load 177 and a ground 179. In some embodiments, fluorolucent magnetic transmitting elements can each be driven by a separate drive circuit 152.

As discussed, the Howland current source 164 can be modified by introducing a phase lead via the phase lead capacitor 175 to achieve a high output impedance as measured at the input to the fluorolucent magnetic transmitting element 169, while driving a flat coil load (e.g., fluorolucent magnetic transmitting element). In some embodiments, the high output impedance can be defined as an impedance in a range from 10 kilohms to 100 kilohms. However, the impedance can be less than 10 kilohms or greater than 100 kilohms. By achieving a high output impedance, coupling between neighboring magnetic transmitting elements (e.g., copper coils) can be reduced. For example, driving the fluorolucent magnetic transmitting element at high impedance can cause the fluorolucent magnetic transmitting element to be less susceptible to coupling with the neighboring magnetic transmitting elements. For example, as an impedance that each fluorolucent magnetic transmitting element is driven at increases, frequencies radiating from the neighboring magnetic transmitting elements are less likely to re-radiate from the fluorolucent magnetic transmitting element.

Because the phase lead capacitor 175 is a function of amplifier performance as well as load, the recommended procedure to affix an appropriate value for the phase lead capacitor can be to run a simulation program with integrated circuit emphasis (SPICE) simulation model using accurate models for the amplifiers, as well as measured values of inductance and resistance for the coil (load). Output impedance can be assessed in the Spice simulation by shorting the input 154 ($V_{in}$) to circuit ground, and connecting a current source with a magnitude ($I_L$) to the load set at the desired drive frequency. The resultant output voltage ($V_o$) on the load then allows the output impedance ($Z_o$) to be calculated: $Z_o = V_o/I_L$. The phase lead capacitor can be adjusted to maximize $Z_o$. Even with the high current output amplifier and a frequency of 10 kilohertz, an output impedance of 40 kilohms can be realized.

Figure 8:
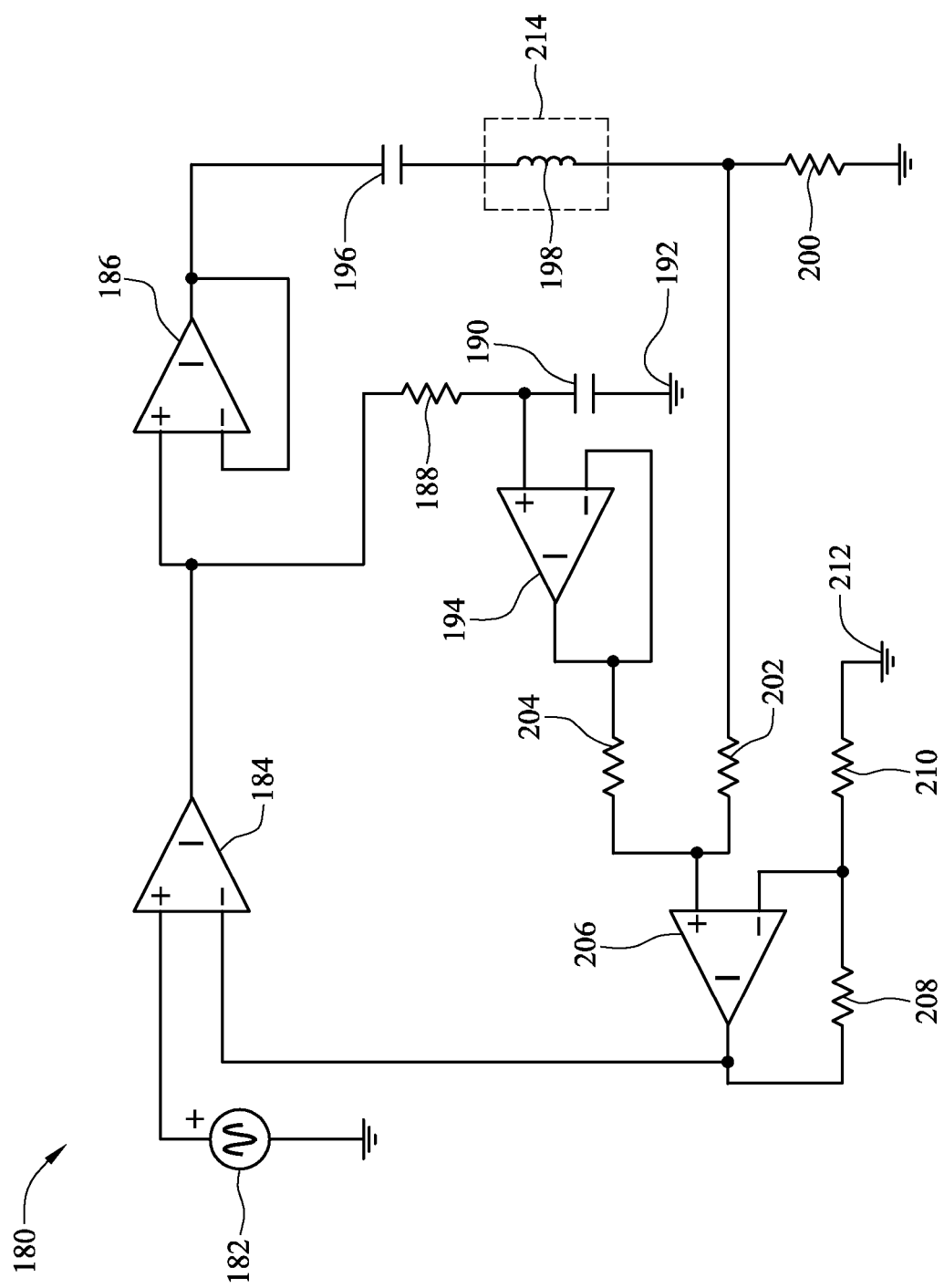
FIG. 8 depicts a schematic view of a second embodiment of a drive circuit for a fluorolucent magnetic transmitting element, in accordance with embodiments of the present disclosure.

FIG. 8 depicts a schematic view of a second embodiment of a drive circuit 180 for a fluorolucent magnetic transmitting element, in accordance with embodiments of the present disclosure. An alternate drive circuit to the drive circuit 152 (depicted in FIG. 7) is depicted in FIG. 8. This drive circuit 180 makes use of a current feedback loop to ensure that the current through the coil stays constant. Additionally, a second feedback loop is used for DC closure. The advantage of this method over the earlier modified Howland circuit 152 is the output impedance is not dependent on the matching resistors and there is no output resistor (other than a small sense resistor and the intrinsic resistance of the flat coil) that otherwise dissipates power. It can be desirable that the output impedance is not dependent on matching resistors because matching can require time and money and can introduce variability as the electrical characteristics change with temperature and age. Designs that do not require matching resistors may be easier to manufacture and can have a greater reliability.

Some embodiments can include a method for preventing coil to coil coupling in an array of magnetic transmitting elements. In some embodiments, the method can include providing a reference signal to a magnetic transmitting element and a low pass filter in parallel. For example, in some embodiments, the reference signal can include an alternating current (e.g., sine waveform) that can be supplied to the drive circuit 180 via an input signal source 182 at a desired frequency (or frequencies). The input signal source 182 can provide a reference signal used to generate a desired signal driven through a fluorolucent magnetic transmitting element 214, as further discussed below. As depicted in FIG. 8, the ground 181 represents a signal reference for the depicted drive circuit 180.

In some embodiments, the reference signal, which can include a sine wave, can be generated by a digital-to-analog converter (not shown). The sine wave can be represented as a 10 kilohertz (kHz) source for example purposes. The sine wave can be driven into a non-inverting input of a first operational amplifier 184. However, the sine wave can have a frequency greater than or less than 10 kHz. For example, the sine wave can have a frequency in a range from 1 to 20 kilohertz. In some embodiments, the sine wave can have a frequency less than 1 kilohertz or greater than 20 kilohertz. For example, the circuit can scale to frequencies less than 1 kilohertz or greater than 20 kilohertz based on circuit components that are selected.

An output of the first operational amplifier 184 can be driven into a buffer circuit, which can be a second operational amplifier 186 that is configured for unity gain. An output from the first operational amplifier 184 also drives a low pass filter circuit, which includes a first resistor 188 and a first capacitor 190, which leads to a ground 192. The first resistor 188 can have a resistance of approximately 100 kilohms, although the first resistor 188 can have a resistance less than or greater than 100 kilohms. The first capacitor 190 can have a capacitance of approximately 0.1 microfarad, although the first capacitor 190 can have a capacitance less than or greater than 0.1 microfarad. In some embodiments, the capacitance of the first capacitor 190 can be determined based on the frequency of the input signal source 182 in order to provide a desired attenuation. The low pass filter (e.g., resistor-capacitor circuit) can filter the 10 kilohertz signal such that only a direct current value remains.

The direct current value (e.g., direct current offset) may ideally be zero, but may have a small value due to less than ideal circuit behavior. The direct current value ($V_{DC}$) can be buffered by a third operational amplifier 194 that is configured for unity gain. In some embodiments, the direct current value (e.g., direct current offset) can provide a reference for how much attenuation needs to be performed to the reference signal, as previously discussed, that has passed through the magnetic transmitting element. The signal generated by the low pass filter that is buffered by the third operational amplifier 194 provides for direct current loop closure and a direct current offset with respect to the reference signal.

In some embodiments, the buffer circuit (e.g., second operational amplifier 186 configured for unity gain) can drive a second capacitor 196 in series with a flat coil load 198 and a sense resistor 200. In some embodiments, the flat coil load can be representative of a fluorolucent magnetic transmitting element 214, as discussed herein. The second capacitor's 196 capacitance can be chosen such that it approximately offsets a reactive impedance of the flat coil load 198, such that a phase angle of a driving circuit of the flat coil load 198 is approximately zero. As depicted in FIG. 8, the fluorolucent magnetic transmitting element 214 is depicted without a resistance. In practice, components of the fluorolucent magnetic transmitting element 214 will have some parasitic component (e.g., resistance); however, for illustration purposes the fluorolucent magnetic transmitting element is depicted without an associated resistance.

In some embodiments, the second capacitor 196 does not have to have a precise capacitance value. The sense resistor 200 can be a current sense resistor with approximately 1 Ohm of resistance and can sense the reference signal that has passed through the fluorolucent magnetic transmitting element, although the sense resistor 200 can have a resistance less than or greater than 1 Ohm. In some embodiments, at least one of a voltage, current, and phase of the reference signal that has passed through the fluorolucent magnetic transmitting element can be sensed. A voltage and phase measured at the sense resistor 200 ($V_{SENSE}$) can correspond to a current and phase of the flat coil load 198. In some embodiments, this signal is fed back to a third resistor 202 where it is summed with the direct current offset from a fourth resistor 204 to generate an attenuation term and subsequently fed to a fourth operational amplifier 206. The fourth operational amplifier 206 can be configured as a non-inverting summing amplifier. The output of the fourth operational amplifier 206 can be defined through the following equation:

$$V_{U4}=1+(R6/R5)*((V_{SENSE}+V_{DC})/2)$$

where $V_{U4}$ is a voltage output of the fourth operational amplifier 206. R6 is a resistance of a sixth resistor 208 that is electrically connected between an output of the fourth operational amplifier 206 and an inverting input of the fourth operational amplifier 206. R5 can be a resistance of a fifth resistor 210 electrically connected between the inverting input of the fourth operational amplifier 206 and a ground 212. $V_{SENSE}$ can be a voltage and phase measured at the sense resistor 200 and $V_{DC}$ can be the direct current value. In some embodiments, the resistance of the sixth resistor 208 can be 5 kilohms and the resistances of the third resistor 202, fourth resistor 204, and the fifth resistor 210 can be 1 kilohms each, although the resistances of the sixth resistor 208, third resistor 202, fourth resistor 204, fifth resistor 210, and sixth resistor 208 can be less than or greater than those resistances discussed herein.

In some embodiments, the output of the fourth operational amplifier 206 can be electrically connected to an inverting input of the first operational amplifier 184 to close the control loop and to apply the attenuation term to the reference signal to attenuate the reference signal. Thus, the output of the fourth operational amplifier 206 can follow the sine wave input in amplitude and phase, as the control loop can force the voltage sensed at the sense resistor 200 to proportionally follow the sine wave input. This can effectively drive out any currents that have been coupled from adjacent flat coils. By adjusting resistor values and/or the sine wave input amplitude, current through the flat load coil 198 can be set to a desired value.

Figure 9:
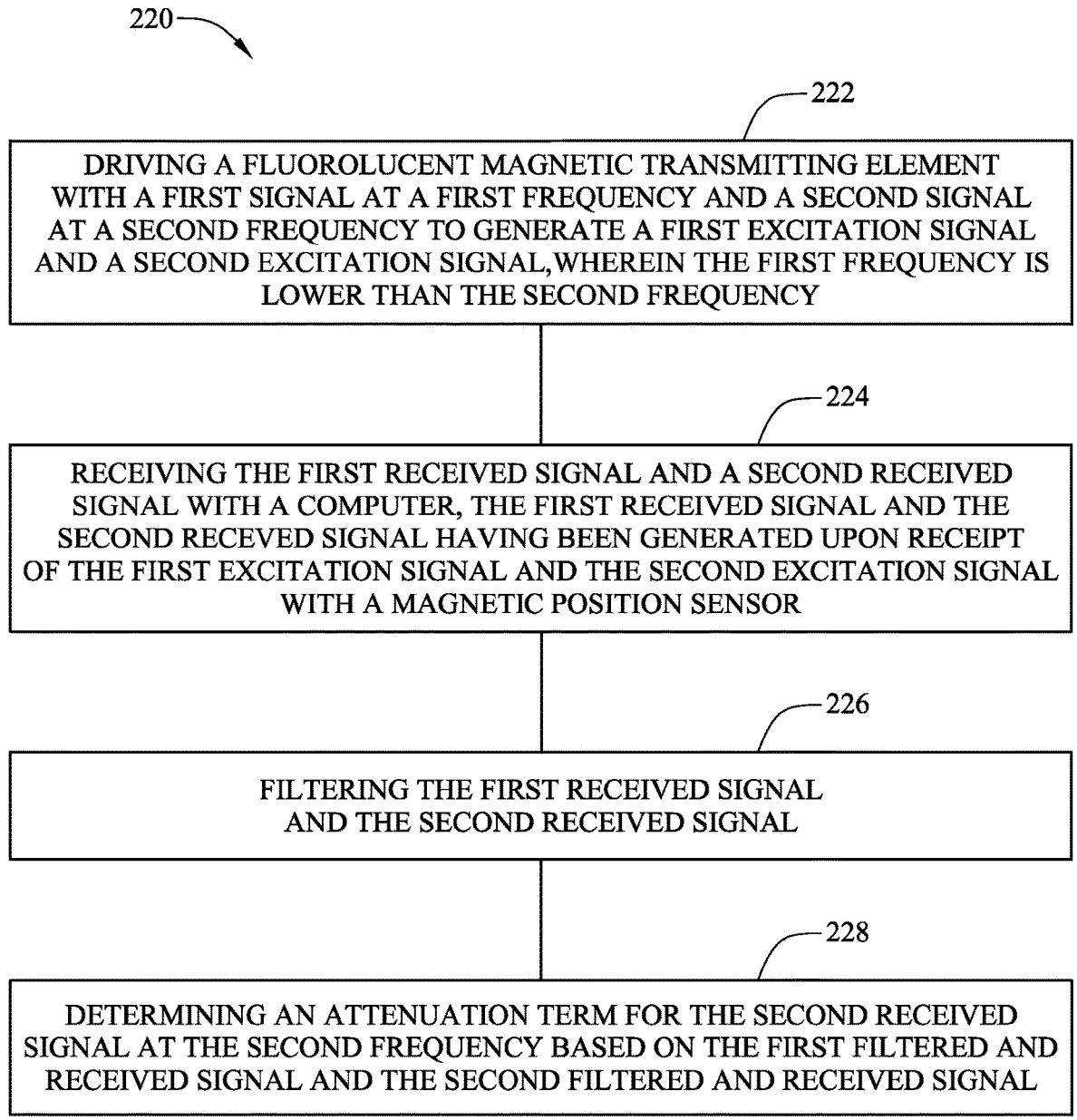
FIG. 9 depicts a block diagram for a method for determining an attenuation term for a signal produced by a fluorolucent magnetic transmitting element, in accordance with embodiments of the present disclosure.

FIG. 9 depicts a method 220 for determining an attenuation term for an excitation signal produced by a fluorolucent magnetic transmitting element, in accordance with embodiments of the present disclosure. The method can include driving a fluorolucent magnetic transmitting element with a first signal at a first frequency and a second signal at a second frequency, wherein the first frequency is lower than the second frequency, at block 222. In some embodiments, the first signal can be a low frequency signal in a range from 0.5 kilohertz to 2 kilohertz and the second frequency can be a high frequency signal in a range from 10 kilohertz to 20 kilohertz; and the first and second signal can be used to drive each fluorolucent magnetic transmitting element. In some embodiments where more than one fluorolucent magnetic transmitting element is being driven, each transmitting element can be driven at a low and high frequency, however, the low and high frequency at which each transmitting element is driven can be unique to each transmitting element. For instance, where two transmitting elements are being driven with low and high frequencies, the low frequencies can be different from one another and the high frequencies can be different from one another.

Alternatively, as previously discussed, more than two signals can be used to drive each fluorolucent magnetic transmitting element. Upon driving the fluorolucent magnetic transmitting element(s) with the first and second signals, a first excitation signal (e.g., first magnetic field) can be generated by each fluorolucent magnetic transmitting element and a second excitation signal (e.g., second magnetic field) can be generated by each fluorolucent magnetic transmitting element, respectively. In some embodiments, a first received signal and a second received signal can be generated upon receipt of the first excitation signal and the second excitation signal with a magnetic position sensor (e.g., a magnetic coil, a wound coil). The method can include receiving the first received signal and the second received signal with a computer, at block 224.

The low frequency component and the high frequency component of the first received signal and the second received signal can be separated since the received signals can be combined on receipt with the magnetic position sensor. Separation of the signal components can allow for each received signal component to be analyzed separately. In an example, the low frequency and high frequency components of the received signals can be separated by frequency domain multiplexing, in some embodiments. In some embodiments, a lower frequency (e.g., 1 kilohertz) signal can remain relatively unperturbated by a number of structural materials (e.g., metallic elements), as further discussed in relation to FIG. 10, the lower frequency signal can be used to calibrate a higher frequency signal, which can be used for navigation. The higher frequency signal can have a greater responsiveness for navigation, but can be perturbated by metallic elements (e.g., aluminum, copper, thin steel, thick steel); while the lower frequency signal can cause a more sluggish performance when used for navigation. By way of example, a lower frequency signal is referred to herein as being a signal with a frequency of 1 kilohertz and a higher frequency signal is referred to herein as being a signal with a frequency of 10 kilohertz. However, the lower frequency can have a frequency in a range from 0.5 kilohertz to 2 kilohertz and the higher frequency signal can have a frequency in a range from 10 kilohertz to 20 kilohertz, as previously discussed.

Figure 10:
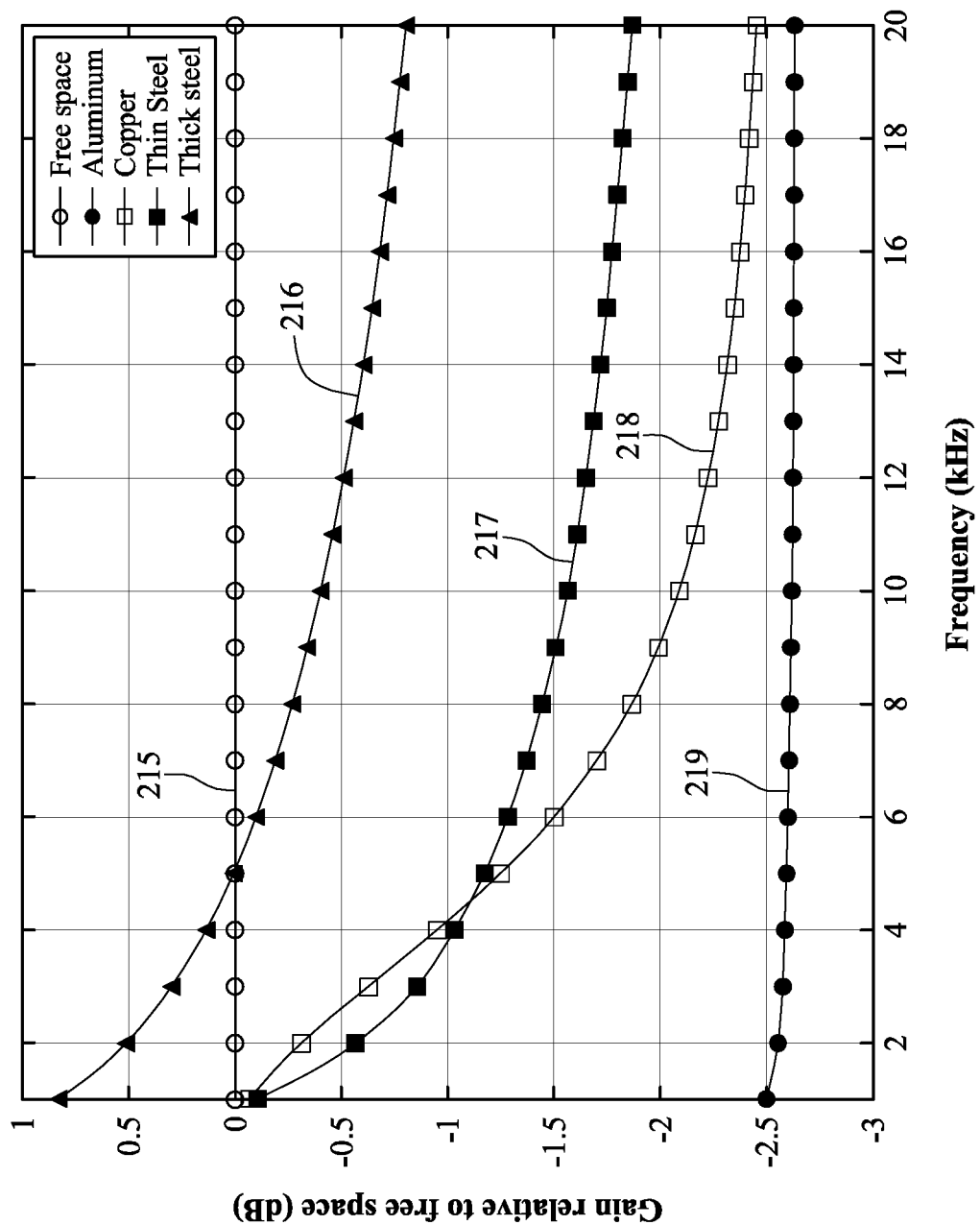
FIG. 10 depicts a graph showing a non-linear frequency-dependent attenuation of a signal generated by a magnetic position sensor due to the presence of various metals with respect to free space, in accordance with embodiments of the present disclosure.

To further illustrate this, FIG. 10 depicts a graph showing a non-linear frequency-dependent attenuation of a signal generated by a magnetic position sensor in the presence of various metals with respect to free space (e.g., air), in accordance with embodiments of the present disclosure. FIG. 10 is experimental data associated with a non-linear frequency-dependent attenuation of a signal generated by a magnetic position sensor in the presence of various metals with respect to free space. The attenuation can be defined as a change in an induced voltage relative to free space at the same frequency. As used herein, perturbation can be defined as a non-linear frequency-dependent attenuation of a signal generated by a magnetic position sensor in the presence of various metals with respect to free space.

As depicted, a lower frequency (e.g., 1 kilohertz) can remain relatively unperturbated by the metallic elements (e.g., aluminum, copper, thin steel, thick steel). The thin steel was between 0.025 and 0.1 millimeters thick and the thick steel was approximately 2 centimeters thick. As depicted, while the signal is less perturbated by aluminum than the other metallic elements, the signal still becomes perturbated as the frequency increases. An even more pronounced perturbation is noticed with regard to copper, thin steel, and thick steel when present in a magnetic field. For instance, as the frequency increases, the perturbation of the signal increases. In an example, with reference to FIG. 10, relative to free space data set 215, a thick steel data set 216 experiences a similar amount of frequency attenuation as that of a thin steel data set 217 and a copper data set 218. With reference to the aluminum data set 219, the data experiences the least amount of frequency attenuation relative to the free space data set 215.

Challenges can exist when using a lower frequency (e.g., 1 kilohertz) signal for navigation. For example, a greater current can be provided to the fluorolucent magnetic transmitting element, as opposed to using a higher frequency (e.g., 10 kilohertz), or a greater area associated with coils of the fluorolucent magnetic transmitting element can be required. Alternatively, to navigate with a same sort of responsiveness as a higher frequency (e.g., 10 kilohertz), signal filtering can be performed on the lower frequency signal (e.g., first received signal) to remove noise from the signal. However, filtering of the lower frequency signal can result in a sluggish performance due to the resources and time required for filtering. In accordance with embodiments of the present disclosure, filtering can be performed on the lower frequency signal received by the position sensor 28 not for navigation purposes, but for calibrating the higher frequency signal (e.g., second signal) to a metallic environment in proximity to the navigational field.

As depicted in FIG. 10, a voltage induced on a position sensor (e.g., position sensor $28_1$ in FIG. 1A and 1B) is a linear function of a magnetic frequency. While 1 kilohertz magnetic fields can become less perturbated than 10 kilohertz fields, 10 times the current and consequently 100 times the power dissipation are required to obtain the same voltage induced on the position sensor 28 with a 1 kilohertz field versus a 10 kilohertz field.

Due to the low inductance of some fluorolucent magnetic transmitting elements (e.g., a flat drive coil such as that discussed in relation to FIG. 3C), multiple frequencies can be driven through a single fluorolucent transmitting element simultaneously, with a unique pair of frequencies (e.g., two frequencies) used for each fluorolucent magnetic transmitting element. However, in some embodiments, greater than two frequencies can be driven through each fluorolucent transmitting element simultaneously. For example, four or more frequencies can be used to drive the single fluorolucent transmitting element simultaneously, which can improve a robustness associated with determining a position of a magnetic position sensor and in calculation of an attenuation term; the calculation of which is further discussed herein. In an example, the frequency dependence of the attenuation can be described parametrically, so additional measurements (e.g., measurements gathered through additional frequencies that are used to drive the fluorolucent magnetic transmitting element) can provide a more robust estimate of the attenuation.

In some embodiments, a low inductance of the fluorolucent magnetic transmitting element can in a range from 0.1 millihenry to 4 millihenry or in a range from 0.1 to 2 millihenry. This is in contrast to a more traditional transmitter coil (e.g., copper coil), which can prove to be more difficult to drive multiple frequencies through the coil, since it is of a higher inductance than the fluorolucent magnetic transmitting element. For example, a more traditional transmitter coil can have an inductance in a range from 15 millihenry to 50 millihenry.

With further reference to FIG. 9, in some embodiments, the method 220 can include filtering the first received signal and the second received signal, at block 226, to provide a first filtered and received signal and a second filtered and received signal. In an example, the first received signal (e.g., low frequency signal) and the second received signal (e.g., high frequency signal) can be filtered based on a signal to noise ratio. For instance, the first signal can be highly filtered to achieve an acceptable signal to noise ratio and can be used to dynamically calibrate the higher frequency signal, which can be used to provide accurate navigation of the position sensor 28. For example, the first signal can be used to continuously calibrate the higher frequency signal. In some embodiments, the signal to noise ratio can be in a range from 30 to 90 decibels. In some embodiments, the signal to noise ratio can be in a range from 40 to 70 decibels. In some embodiments, the signal to noise ratio can be 45 decibels. The low frequency signal can be used to probe a navigational domain and can rely on the fact that the low frequency is relatively unperturbated by the number of structural materials (e.g., metallic objects) that can otherwise impact the high frequency signal.

In an example, a 10 kilohertz signal can inherently have 10 times the recovered signal amplitude and thus 10 times the signal-to-noise ratio of the 1 kilohertz signal, assuming the drive coils are driven with identical amplitudes for each frequency. However, in some embodiments, because the 1 kilohertz signal can be used for a more static or regional calibration factor, it can be conventionally time domain filtered in a range from 1/10 to 1/100 the bandwidth of the dynamic location result obtained from the 10 kilohertz signal, thus yielding a suitable or equivalent signal to noise ratio. The heavier filtering can be used on the 1 kilohertz signal because it only needs to adapt to generally infrequent perturbations in the magnetic field (e.g., caused by a change in fluoroscopy head position). A filter settling time of 1 to 3 seconds can be used following such a perturbation. Alternatively, an optimal filter using statistical methods such as a Kalman filter that accounts for the higher noise level of the 1 kilohertz signal can be used to combine the information from both the 1 kilohertz signal and the 10 kilohertz signal.

As the structural materials move with respect to the navigational domain (e.g., area of interest 38 (FIG. 2)), filtering can be performed on the low frequency signal and the high frequency signal and the filtered low frequency signal and the filtered high frequency signal can be used to determine an attenuation term (further defined below) for the higher frequency signal for use in navigation. For example, the method 220 (FIG. 9) can include determining an attenuation term for the second signal at the second frequency based on the first filtered and received signal and the second filtered and received signal, at block 228.

In some embodiments, the first received signal and the second received signal can remain unfiltered when determining the attenuation term for the second signal at the second frequency. Upon determination of the attenuation term from the unfiltered signals, the attenuation term can be filtered to provide a filtered attenuation term. In some embodiments, this can save processing resources associated with a computer by allowing for one input to be filtered (e.g., the attenuation term) and avoiding the filtering of two or more inputs (e.g., first signal, second signal). In cases where more than two signals are used, this can prove to be especially true.

In some embodiments, the attenuation term can be defined via the following equation, $$(V_2 * \omega_1)/(V_1 * \omega_2)$$

where $V_1$ is representative of a first voltage amplitude induced in a coil associated with the first signal; $V_2$ is representative of a second voltage amplitude induced in a coil associated with the second signal; $\omega_1$ is representative of a first frequency associated with the first signal; and $\omega_2$ is representative of a second frequency associated with the second signal. As depicted and discussed in relation to FIG. 8, the attenuation term can be applied to the reference signal via the fourth operational amplifier 206 to attenuate the reference signal. Accordingly, the method can include determining the attenuation term for the second received signal at the second frequency based on the first filtered and received signal and the second filtered and received signal. For example, with reference to the above equation, the attenuation term can be determined based on a first voltage amplitude induced in the fluorolucent magnetic transmitting element associated with the first signal and a first frequency associated with the first signal; and a second voltage amplitude induced in the fluorolucent magnetic transmitting element associated with the second signal and a second frequency associated with the second signal. In an ideal system (e.g., in free-space) where the first frequency and second frequency are unperturbated, the attenuation term can be one. However, where perturbations are present, the attenuation term can be greater than or less than one.

As a structural material (e.g., magnetic field-disturbing object, metallic object) moves within proximity of the navigational domain, a position determined from the first signal (e.g., lower frequency signal) that is received by the position sensor $28_1$ (FIGS. 1A and 1B) can remain approximately the same, while a position determined from the second signal (e.g., higher frequency signal) that is received by the position sensor $28_1$ can change. Based on the change in position and/or change in a voltage induced in the position sensor $28_1$ via the first received signal versus a voltage induced in the position sensor $28_1$ via the second received signal, the second received signal can be calibrated. For example, an attenuation term can be determined, as previously discussed, which can be used to calibrate the second received signal. In some embodiments, the attenuation term can be applied to the second received signal to factor out perturbations in the second received signal (e.g., perturbations caused by structural materials such as metallic objects). In some embodiments, the attenuation term can be applied to the second received signal by dividing the second received signal by the attenuation term.

As previously discussed, the attenuation term can be filtered in some embodiments, thus alleviating the need to individually filter the first received signal and the second received signal. Upon filtering of the attenuation term, the attenuation term can be referred to herein as a filtered attenuation term. In some embodiments, the filtered attenuation term can be applied to the second received signal to compensate the second received signal for a perturbation in the second received signal. Upon application of the filtered attenuation term to the second received signal, the second received signal can be referred to as an attenuated received signal. The filtered attenuation term can be applied to the second received signal by dividing the second received signal by the filtered attenuation term to provide the attenuated received signal.

In some embodiments, each received signal can be analyzed to determine the respective frequency associated with each received signal and a statistical filter can be used along with both high frequency and low frequency measurements to determine a high frequency gain relative to free-space. In some embodiments, the filter can be a Kalman filter. As such, corrections can be made for perturbations in tracking accuracy when metallic objects, such as the C-arm, x-ray emitter, x-ray detector, etc. are moved in a proximity to the navigational domain. In some embodiments, as previously discussed, using the low frequency signal alone for navigation purposes can result in sluggish performance due to the amount of filtering that is performed on the low frequency signal (e.g., due to a group delay associated with low-pass filtering). However, by the time a magnetic field-disturbing object is moved with respect to the navigational domain (e.g., area of interest 38 (FIG. 2)), the low frequency signal can be filtered and the higher frequency signal can be adjusted, based on the filtered low frequency signal, to account for any magnetic disturbance caused by the metallic object.

In some embodiments where the first received signal and the second received signal are filtered, the second filtered and received signal can be adjusted by applying the attenuation term to the second filtered and received signal (e.g., by dividing the second filtered and received signal by the attenuation term) to provide an adjusted second signal compensated for perturbations via the attenuation term. A position associated with the magnetic position sensor can then be determined based on the adjusted second signal (e.g., attenuated received signal).

Figure 11:
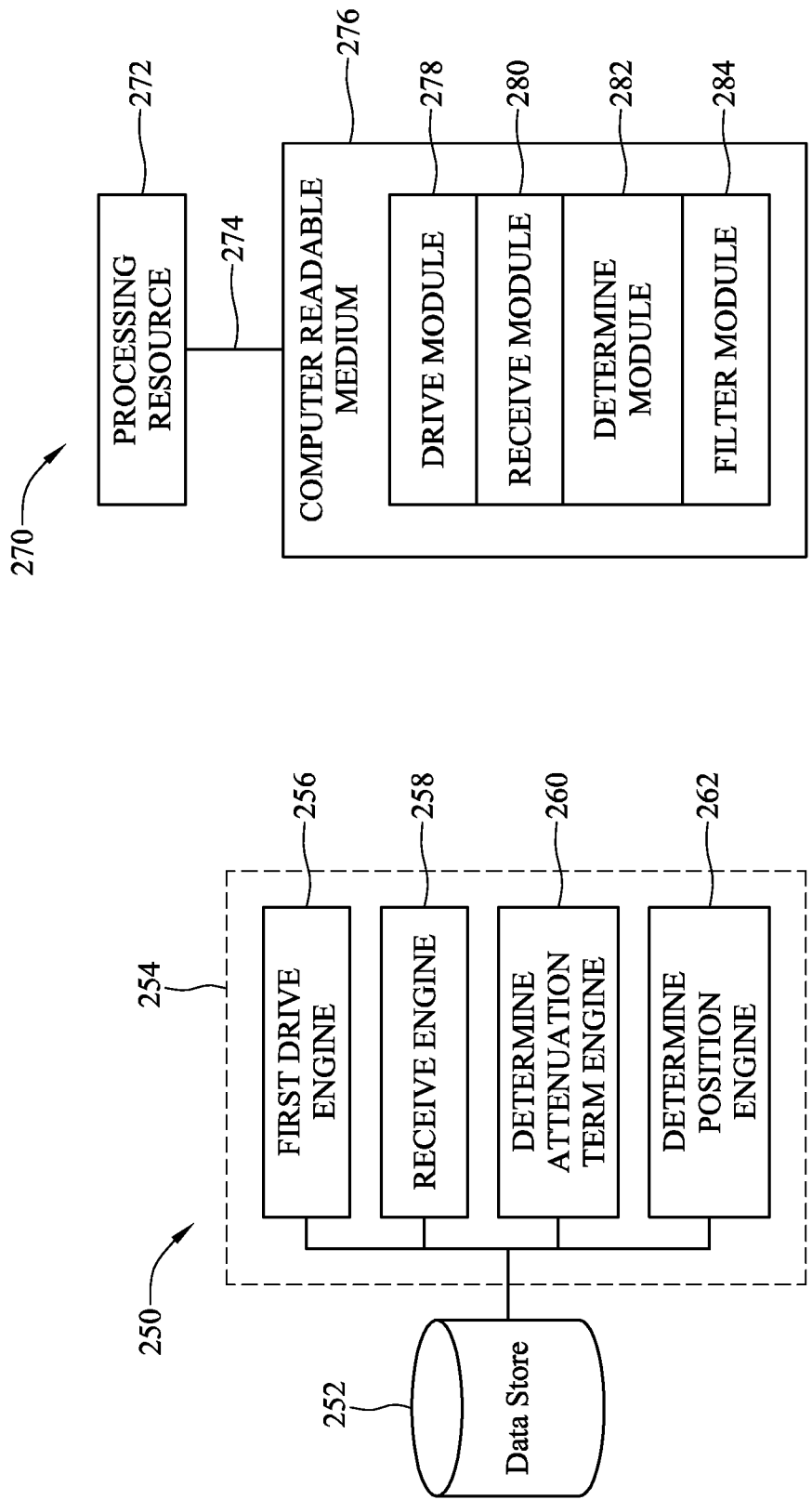
FIG. 11A depicts a diagram of a system for determining an attenuation term for a signal produced by a fluorolucent magnetic transmitting element, according to embodiments of the present disclosure.
FIG. 11B depicts a diagram of an example of a computing device for determining an attenuation term for a signal produced by a fluorolucent magnetic transmitting element, according to various embodiments of the present disclosure.

FIG. 11A depicts a diagram of a system 250 for determining an attenuation term for a signal produced by a fluorolucent magnetic transmitting element, according to embodiments of the present disclosure. The system 250 can include a data store 252, a determining attenuation term sub-system 254, and/or a number of engines. The determining attenuation term sub-system 254 can be in communication with the data store 252. The determining attenuation term sub-system 254 can include a number of engines (e.g., drive engine 256, receive engine 258, determine attenuation term engine 260, determine position engine 262, etc.). The determining attenuation term sub-system 254 can include additional or fewer engines than illustrated to perform the various functions described herein. The number of engines can include a combination of hardware and programming configured to perform a number of functions described herein (e.g., receiving, determining, etc.). Each of the engines can include hardware or a combination of hardware and programming designated or designed to execute a module (e.g., a particular module). The programming can include instructions (e.g., software, firmware, etc.) stored in a memory resource (e.g., computer-readable medium) as well as a hard-wired program (e.g., logic).

The determining attenuation term sub-system 254 can include a computing device analogous to that discussed herein and with respect to FIG. 11B, which is further discussed below. In some embodiments, the computing device can include a digital display such as a graphical user interface (GUI), which is suitable for the display of electronic data. A user interface can include hardware components and/or computer-readable instruction components. For instance, hardware components can include input components (e.g., a mouse, a touchscreen, a keyboard, dials and buttons, etc.) and/or output components (e.g., a display, vibration generating devices, speakers, etc.). An example user interface can include a GUI, which can digitally represent data associated with determining an attenuation term for a signal produced by a fluorolucent magnetic transmitting element.

The drive engine 256 can include hardware and/or a combination of hardware and programming to drive the fluorolucent magnetic transmitting element with a first signal at a first frequency and a second signal at a second frequency to generate a first excitation signal and a second excitation signal, wherein the first frequency is lower than the second frequency. In some embodiments, as discussed herein, the lower frequency signal (e.g., first signal) can have a frequency in a range from 0.5 kilohertz to 2 kilohertz and the higher frequency signal (e.g., second signal) can have a frequency in a range from 10 kilohertz to 20 kilohertz. The lower frequency at which the first excitation signal is generated can remain relatively unperturbed by metallic elements (e.g., aluminum, copper, thin steel, thick steel) and can thus be used to calibrate the higher frequency excitation signal. In an example, the first excitation signal can be less perturbated by metallic element(s) located proximate to the fluorolucent magnetic transmitting element than the second excitation signal. For instance, the first excitation signal can be less perturbated by a C-arm, x-ray emitter, x-ray detector, etc. located proximate to the fluorolucent magnetic transmitting element.

The receive engine 258 can include hardware and/or a combination of hardware and programming to receive a first received signal and a second received signal with a computer, the first received signal and the second received signal having been generated upon receipt of the first excitation signal and the second excitation signal with a magnetic position sensor. In some embodiments, the magnetic position sensor can be disposed on a catheter (e.g., distal end of a catheter). The magnetic position sensor can be configured to receive the first excitation signal and the second excitation signal generated by the fluorolucent magnetic transmitting element.

The determine attenuation term engine 260 can include hardware and/or a combination of hardware and programming configured to determine an attenuation term for the second received signal at the second frequency based on the first received signal and the second received signal, as previously discussed herein. In some embodiments, the attenuation term for the second signal can be determined based on a change in position and/or change in a voltage induced in the magnetic position sensor via the first received signal versus a change in position and/or a voltage induced in the magnetic position sensor via the second received signal, as discussed herein.

The determine position engine 262 can include hardware and/or a combination of hardware and programming configured to determine a position of the magnetic position sensor based on an attenuated received signal, the attenuated received signal having been generated through application of the attenuation term to the second received signal. In some embodiments, a position of the magnetic position sensor determined based on the attenuated received signal can be different than a position of the magnetic position sensor determined based on the second received signal. For example, the position of the magnetic position sensor determined based on the attenuated received signal can be corrected for perturbations caused in the magnetic field as a result of the attenuation term being applied to the second received signal.

As discussed herein, the first excitation signal, which can be generated via a lower frequency than the second signal, can be less perturbated by a metallic object located proximate to the fluorolucent magnetic transmitting element than the second excitation signal. In some embodiments, a frequency associated with the first signal can be in a range from 0.5 to 2 kilohertz and a frequency associated with the second signal can be in a range from 10 to 20 kilohertz.

FIG. 11B depicts a diagram of an example of a computing device 270 for determining an attenuation term for a signal produced by a fluorolucent magnetic transmitting element, according to various embodiments of the present disclosure. The computing device 270 can utilize software, hardware, firmware, and/or logic to perform a number of functions described herein.

The computing device 270 can be a combination of hardware and instructions to share information. The hardware, for example can include a processing resource 272 and/or a memory resource 276 (e.g., computer-readable medium (CRM), database, etc.). A processing resource 272, as used herein, can include a number of processors capable of executing instructions stored by the memory resource 276. Processing resource 272 can be integrated in a single device or distributed across multiple devices. The instructions (e.g., computer-readable instructions (CRI)) can include instructions stored on the memory resource 276 and executable by the processing resource 272 to implement a desired function (e.g., determine an attenuation term for the second received signal at the second frequency based on the first received signal and the second received signal, etc.).

The memory resource 276 can be in communication with the processing resource 272. The memory resource 276, as used herein, can include a number of memory components capable of storing instructions that can be executed by the processing resource 272. Such memory resource 276 can be a non-transitory CRM. Memory resource 276 can be integrated in a single device or distributed across multiple devices. Further, memory resource 276 can be fully or partially integrated in the same device as processing resource 272 or it can be separate but accessible to that device and processing resource 272. Thus, it is noted that the computing device 270 can be implemented on a support device and/or a collection of support devices, on a mobile device and/or a collection of mobile devices, and/or a combination of the support devices and the mobile devices.

The memory 276 can be in communication with the processing resource 272 via a communication link 274 (e.g., path). The communication link 274 can be local or remote to a computing device associated with the processing resource 272. Examples of a local communication link 274 can include an electronic bus internal to a computing device where the memory resource 276 is one of a volatile, non-volatile, fixed, and/or removable storage medium in communication with the processing resource 272 via the electronic bus.

Link 274 (e.g., local, wide area, regional, or global network) represents a cable, wireless, fiber optic, or remote connection via a telecommunication link, an infrared link, a radio frequency link, and/or other connectors or systems that provide electronic communication. That is, the link 274 can, for example, include a link to an intranet, the Internet, or a combination of both, among other communication interfaces. The link 274 can also include intermediate proxies, for example, an intermediate proxy server (not shown), routers, switches, load balancers, and the like.

The memory resource 276 can include a number of modules such as a drive module 278, a receive module 280, a determine module 282, and a filter module 284. The modules 278, 280, 282, 284 can include CRI that when executed by the processing resource 272 can perform a number of functions. The modules 278, 280, 282, 284 can be sub-modules of other modules. For example, the drive module 278 and the receive module 280 can be sub-modules and/or contained within the same computing device. In another example, the modules 278, 280, 282, 284 can comprise individual modules at separate and distinct locations (e.g., CRM, etc.).

Each of the modules 278, 280, 282, 284 can include instructions that when executed by the processing resource 272 can function as a corresponding engine, as described herein. For example, the determine attenuation term module 282 can include CRI that when executed by the processing resource 272 can function as the determine attenuation term engine 260. For instance, the determine attenuation term module 282 can include CRI that when executed by the processing resource 272 can cause a computing device to determine an attenuation term for the second received signal at the second frequency based on the first received signal and the second received signal.

Figure 12:
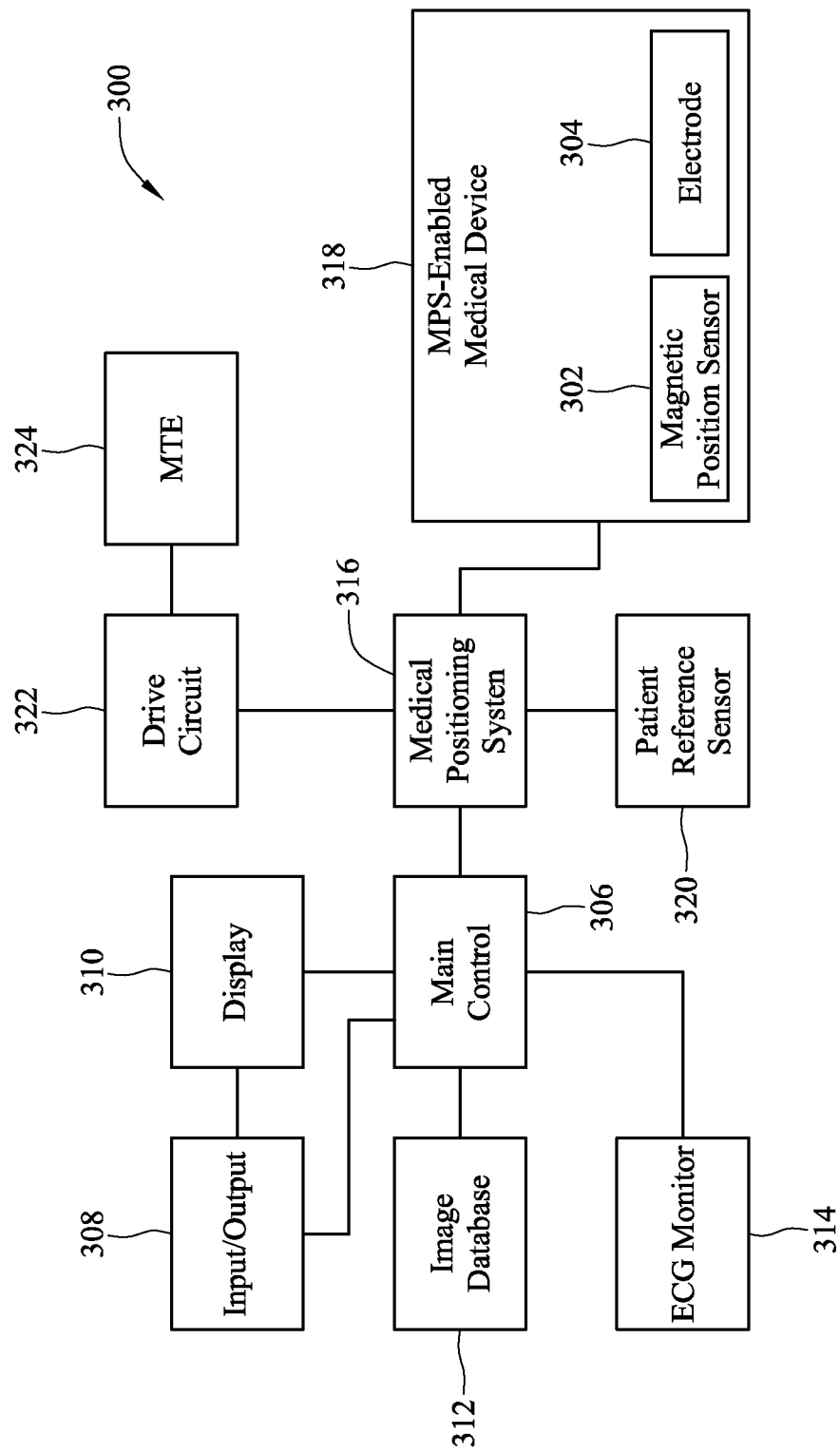
FIG. 12 depicts a schematic and block diagram view of an electromagnetic navigation system, in accordance with embodiments of the present disclosure.

FIG. 12 depicts a schematic and block diagram view of an electromagnetic navigation system 300, in accordance with embodiments of the present disclosure. The electromagnetic navigation system 300 can be a system in which a medical device, such as a guidewire, catheter, introducer (e.g., sheath) incorporating a magnetic position sensor 302 and/or an electrode 304 may be used. With continued reference to FIG. 12, system 300, as depicted, includes a main electronic control unit 306 (e.g., a processor) having various input/output mechanisms 308, a display 310, an optional image database 312, an electrocardiogram (ECG) monitor 314, a localization system, such as a medical positioning system 316, a medical positioning system-enabled elongate medical device 318, a patient reference sensor 320, a magnetic position sensor 302 and an electrode 304. For simplicity, one magnetic position sensor 302 and one electrode 304 are shown, however, more than one magnetic position sensor 302 and/or more than one electrode 304 can be included in the system 300.

In some embodiments, the system 300 can include a drive circuit in communication with the medical positioning system 316. The drive circuit 322 can include a drive circuit similar to those discussed herein, for example, those discussed in relation to FIGS. 7 and 8. The drive circuit 322 can be in communication with one or more magnetic transmitting elements (MTE) 324, which in some embodiments can be a fluorolucent magnetic transmitting elements, such as that discussed in relation to FIG. 3C or a non-fluorolucent magnetic transmitting element.

Input/output mechanisms 308 may comprise conventional apparatus for interfacing with a computer-based control unit including, for example, one or more of a keyboard, a mouse, a tablet, a foot pedal, a switch and/or the like. Display 310 may also comprise conventional apparatus, such as a computer monitor.

Various embodiments described herein may find use in navigation applications that use real-time and/or pre-acquired images of a region of interest. Therefore system 300 may optionally include image database 312 to store image information relating to the patient's body. Image information may include, for example, a region of interest surrounding a destination site for medical device 318 and/or multiple regions of interest along a navigation path contemplated to be traversed by medical device 318. The data in image database 312 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus), wherein the image database acts as a buffer (live fluoroscopy); and/or (3) a sequence of related two-dimensional images defining a cine-loop wherein each image in the sequence has at least an ECG timing parameter associated therewith, adequate to allow playback of the sequence in accordance with acquired real-time ECG signals obtained from ECG monitor 314. It should be understood that the foregoing embodiments are examples only and not limiting in nature. For example, the image database may also include three-dimensional image data as well. It should be further understood that the images may be acquired through any imaging modality, now known or hereafter developed, for example X-ray, ultra-sound, computerized tomography, nuclear magnetic resonance or the like.

ECG monitor 314 is configured to continuously detect an electrical timing signal of the heart organ through the use of a plurality of ECG electrodes (not shown), which may be externally-affixed to the outside of a patient's body. The timing signal generally corresponds to a particular phase of the cardiac cycle, among other things. Generally, the ECG signal(s) may be used by the control unit 306 for ECG synchronized play-back of a previously captured sequence of images (cine loop) stored in database 312. ECG monitor 314 and ECG-electrodes may both comprise conventional components. Medical positioning system 316 is configured to serve as the localization system and therefore to determine position (localization) data with respect to one or more magnetic position sensors 302 and/or electrodes 304 and output a respective location reading.

The location readings may each include at least one or both of a position and an orientation (P&O) relative to a reference coordinate system (e.g., magnetic based coordinate system, impedance based coordinate system), which may be the coordinate system of medical positioning system 316. For some types of sensors, the P&O may be expressed with five degrees-of-freedom (five DOF) as a three-dimensional (3D) position (e.g., a coordinate in three perpendicular axes X, Y and Z) and two-dimensional (2D) orientation (e.g., a pitch and yaw) of an electromagnetic position sensor 302 in a magnetic field relative to a magnetic field generator(s) or transmitter(s) and/or electrode 304 in an applied electrical field relative to an electrical field generator (e.g., a set of electrode patches). For other sensor types, the P&O may be expressed with six degrees-of-freedom (six DOF) as a 3D position (e.g., X, Y, Z coordinates) and 3D orientation (e.g., roll, pitch, and yaw).

Medical positioning system 316 determines respective locations (e.g., P&O) in the reference coordinate system based on capturing and processing signals received from the magnetic position sensor 302 while the sensor is disposed in a controlled low-strength alternating current (AC) magnetic (e.g., magnetic) field produced by the MTE 324 and signals received from the electrode 304 while the electrodes are disposed in a controlled electrical field generated by electrode patches, for example. In some embodiments, the medical positioning system 316 and/or the main control 306 can include a computing device, as discussed in relation to FIGS. 11A and 11B, which can include hardware and/or a combination of hardware and programming to determine an attenuation term.

Each magnetic position sensor 302 and the like may comprise a coil and, from an electromagnetic perspective, the changing or AC magnetic field may induce a current in the coil(s) when the coil(s) are in the magnetic field. The magnetic position sensor 302 is thus configured to detect one or more characteristics (e.g., flux) of the magnetic field(s) in which it is disposed and generate a signal indicative of those characteristics, which is further processed by medical positioning system 316 to obtain a respective P&O for the magnetic sensor 302. The electrode 304 may comprise a ring electrode, in some examples. The electrode 304 can be configured to detect one or more characteristics (e.g., current) of the electrical field(s) in which it is disposed and generate a signal indicative of those characteristics, which is further processed by medical positioning system 316 to obtain a respective P&O for the plurality of electrode 304.

Referring still to FIG. 12, in an embodiment, medical positioning system 316 may determine the P&O of medical positioning system enabled medical device 318 according to certain physical characteristics of electromagnetic position sensor 302 and electrode 304 in addition to the signals received from magnetic position sensor 302 and electrode 304. Such characteristics may include predetermined calibration data, for example, indicative of or corresponding to the respective winding angles of one or more portions of a coil on sensor 302, the number of coil portions, the type(s) of conductor used in the coil, and the direction and number of loops in the coil. In addition, such characteristics may include predetermined calibration data, for example, indicative of or corresponding to a position of electrode 304, the number of electrodes 304, size of electrode 304, shape of electrode 304, and type of material(s) the electrodes 304 are formed of. Medical positioning system 316 may have such characteristics of the magnetic position sensor 302 and/or electrode 304 pre-programmed, may determine such characteristics from a calibration procedure, or may receive such characteristics from a storage element coupled with medical device 318.

Magnetic position sensor 302 and the electrode 304 may be associated with medical positioning system enabled medical device 318. Another medical positioning system sensor, namely, patient reference sensor (PRS) 320 (if provided in system 300) can be configured to provide a positional reference of the patient's body so as to allow motion compensation for patient body movements, such as respiration-induced movements. Such motion compensation is described in greater detail in U.S. patent application Ser. No. 12/650,932, entitled "Compensation of Motion in a Moving Organ Using an Internal Position Reference Sensor", hereby incorporated by reference in its entirety as though fully set forth herein. PRS 320 may be attached to the patient's manubrium sternum or other location. Like the magnetic position sensor 302, PRS 320 can be configured to detect one or more characteristics of the magnetic field in which it is disposed, wherein medical positioning system 316 determines a location reading (e.g., a P&O reading) indicative of the PRS's position and orientation in the reference coordinate system. In some embodiments, an additional PRS can be configured to detect one or more characteristics of the electrical field in which it is disposed, wherein the medical positioning system 316 determines a location reading (e.g., a P&O reading) indicative of the PRS's position and orientation in the reference coordinate system.

Embodiments are described herein of various apparatuses, systems, and/or methods. Numerous specific details are set forth to provide a thorough understanding of the overall structure, function, manufacture, and use of the embodiments as described in the specification and depicted in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment of a fluorolucent magnetic field generator has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A fluorolucent magnetic transmitting element for generating a magnetic field for tracking of an object, comprising the following:
   a first spiral arm that extends from a first outer origin inward to a central origin in a first direction, the first spiral arm including a first spiral trace that extends through an interior of the first spiral arm from the first outer origin inward to the central origin in the first direction; and a second spiral arm that extends from the central origin outward to a second outer origin in the first direction, the second spiral arm including a second spiral trace that extends through an interior of the second spiral arm from the central origin outward to the second outer origin in the first direction, wherein:

the first spiral arm and the second spiral arm are formed from an insulative material;

the first spiral trace and the second spiral trace are physically connected at the central origin to form the fluorolucent magnetic transmitting element; and at least a portion of the first spiral arm overlaps at least a portion of the second spiral arm.

2. The fluorolucent magnetic transmitting element of claim 1, wherein the first spiral trace and the second spiral trace are formed from a continuous piece of material.

3. The fluorolucent magnetic transmitting element of claim 2, wherein the continuous piece of material that forms the first spiral trace and the second spiral trace is creased at the central origin.

4. The fluorolucent magnetic transmitting element of claim 3, wherein the continuous piece of material is formed from aluminum.

5. The fluorolucent magnetic transmitting element of claim 1, wherein:

the first spiral trace and the second spiral trace are cut from a planar piece of material; and the first spiral trace and the second spiral trace are creased at the central origin.

6. The fluorolucent magnetic transmitting element of claim 1, wherein a first electrical terminal is disposed on the first spiral trace at the first outer origin and a second electrical terminal is disposed on the second spiral trace at the second outer origin.

7. The fluorolucent magnetic transmitting element of claim 6, wherein the first spiral trace and the second spiral trace are configured to transmit an electrical current from the first electrical terminal to the second electrical terminal in the first direction and to produce a magnetic field.

* * * * *